US006248734B1

(12) United States Patent
Meadows et al.

(10) Patent No.: US 6,248,734 B1
(45) Date of Patent: Jun. 19, 2001

(54) USE OF PHOTODYNAMIC THERAPY FOR PREVENTION OF SECONDARY CATARACTS

(75) Inventors: Howard E. Meadows, Vancouver; Danielle Wenkstern, Lions Bay; David R. Mallek, Vancouver; Marcello Nick Bussanich, Vancouver; Anna M. Richter, Vancouver; Julia G. Levy, Vancouver, all of (CA); Claude A. A. Hariton, Brinckhein (FR); Gustav Huber, Rafz (CH); Jack Rootman, Vancouver (CA)

(73) Assignees: QLT, Inc.; The University of British Columbia, both of (CA); Ciba Vision Opthalmics (CH)

( * ) Notice: Subject to any disclaimer, the term of this patent is extended or adjusted under 35 U.S.C. 154(b) by 0 days.

(21) Appl. No.: 09/536,291

(22) Filed: Mar. 27, 2000

Related U.S. Application Data

(62) Division of application No. 08/762,854, filed on Dec. 10, 1996, now Pat. No. 6,043,237.

(51) Int. Cl.[7] ...................................................... A01N 55/02
(52) U.S. Cl. .............................. 514/185; 514/54; 514/55; 514/912
(58) Field of Search .................................... 514/185, 912, 514/54, 55

(56) References Cited

U.S. PATENT DOCUMENTS

| | | |
|---|---|---|
| 4,920,143 | 4/1990 | Levy et al. . |
| 5,095,030 | 3/1992 | Levy et al. . |
| 5,171,749 | 12/1992 | Levy et al. . |
| 5,202,252 | 4/1993 | Emery et al. . |
| 5,273,751 | 12/1993 | Dubroff . |
| 5,375,611 | 12/1994 | Lindqvist et al. . |
| 5,399,583 | 3/1995 | Levy et al. . |
| 5,401,880 | 3/1995 | Clark et al. . |
| 5,445,637 | 8/1995 | Bretton . |

FOREIGN PATENT DOCUMENTS

| | | |
|---|---|---|
| 0 352 076 | 1/1990 | (EP) . |
| 89/08474 | 9/1989 | (WO) . |
| 95/03797 | 2/1995 | (WO) . |
| 95/24930 | 9/1995 | (WO) . |

OTHER PUBLICATIONS

Apple, D. J. et al., "Posterior Capsule Opacification," *Survey of Ophthalmology*, 37(2):73(1992).
Haimovici, R. et al. "Localization of Benzoporphyrin Derivative Monoacid in the Rabbit Eye," IOVS 34:1303 as Abstracts 2955 (1993).
Kappelhoff, J.P., et al., "The Pathology of After–Cataract. A Mini Review," *Acta Opthalmol.* Suppl. 205:13 (1992).
Li, KF, et al., "514.5nm DHE–PDT and Lens Epithelial Proliferation in vitro: A Pilot Study," *Photochem. Photobiol.*, 51 (Suppl.) Abstract 75s (1990).
Lin, C.P. et al. *IOVS* 34:1168 Abstract 2293 (1993).
Lin, S.C. et al. *IOVS* 34:1303 Abstract 2953 (1993).
Lindquist, B., et al., "Method for Preventing Secondary Cataract," U.S. Patent No. 5,375,611 (1994).
Lingua, R. et al., "Preclinical Evaluation of Photodynamic Therapy to Inhibit Lens Epithelial Proliferation," *Lasers and Light in Ophthalmology* 2(2):103 (1988).
Lundgren, B., et al., "Secondary Cataract: An In vivo Model for Studies on Secondary Cataract in Rabbits," *Acta Opthalmol.* Suppl. 205:25 (1992).
Moulton, R.S. et al. "Response of Retinal and Choroidal Vessels to Photodynamic Therapy Using Benzoporphyrin Derivative Monoacid", IOVS 34:1169 Abstract 58 (1993).
Nishi, O. et al., "Intercapsular Cataract Surgery with Lens Epithelial Cell Removal," *J. Cataract Refract. Surg.* 17:471–477 (1991).
Parel, J–M, et al., "Preclinical Evaluation of Photodynamic Therapy To Retard Lens Epithelial Proliferation After Endocapsular Lensectomy," *Invest Ophthalmo. Visual Sci.*, 28(3):89 (1987).
Parel, J.M. et al., "Endocapsular Lavage with Photofrin II as a Photodynamic Therapy for Lens Epithelial Proliferation," *Lasers and Medical Science* 5:25 (1990).
Schmidt, U. et al. Photosensitizing Potency of Benzoporphyrin Derivative (BPD) Associated with Human Low Density Lipoprotein (LDL). *IOVS* 33:1253 Abstract 2802 (1992).
Schmidt–Erfurth, U. et al. "Photothrombosis of Ocular Neovascularization Using BPD," IOVS 34:1303 as Abstracts 2956 (1993).
Walsh, A.W. et al. Photodynamic Therapy of Experimental Choroidal Neovascularization Using BPD–MA, IOVS 34:1303 as Abstracts 2954 (1993).
Wunderlock, J. et al., "Photodynamic Activity of Phthalocyanines in Cultivated Lens Epithelial Cells of the Pig," *Ophthalmology* 92(3):346 (1995).
Xia, X.P., et al. "A Cytological Study of Inhibition of Secondary Cataract with Heparin," *Chung Hua Yen Ko Tsa Chih*, 30(5):363 (1994).
Xia, X.P., et al. "A Clinical Study of Inhibition of Secondary Cataract with Heparin," *Chung Hua Yen Ko Tsa Chih*, 30(6):405 (1994).

*Primary Examiner*—Zohren Fay
(74) *Attorney, Agent, or Firm*—Morrison & Foerster LLP

(57) ABSTRACT

Photodynamic therapy to prevent secondary cataracts is effected using photosensitizers such as green porphyrins as photoactive agents to destroy remnant lens epithelial cells.

12 Claims, 11 Drawing Sheets

FORMULA 1

FORMULA 2

FORMULA 3

FORMULA 4

FORMULA 5

FORMULA 6

USE OF PHOTODYNAMIC THERAPY FOR PREVENTION OF SECONDARY CATARACTS

This application is a division of U.S. application Ser. No. 08/762,854, filed Dec. 10, 1996, now allowed. Now U.S. Pat. No. 6,043,237.

FIELD OF THE INVENTION

The invention relates to the use of photodynamic therapy treatment (PDT) to prevent secondary cataracts, more particularly to the use of green porphyrins for such PDT treatment.

DESCRIPTION OF THE RELATED ART

The removal of cataracts is one of the most common surgical procedures in the United States. Secondary cataracts, more specifically posterior capsule opacification, are the most common complication of cataract extraction procedures, with or without posterior chamber intraocular lens implantation. Depending on their age, this condition affects from 15–50% of all patients, and generally is "secondary" to a proliferation and migration of residual lens epithelial cells. While ophthalmic surgeons are aware of the incidence of secondary cataracts and take care to remove as many residual lens epithelial cells as possible, e.g., prior to implantation of an artificial intraocular lens, it is difficult to identify all such cells and often difficult to reach them on the inside surface of the lens capsule.

Secondary cataracts, as a post-surgical effect, also are referred to as "after cataract." One commentator has observed that the term "secondary cataract" is ambiguous because it also frequently is used to refer to a cataract that occurs secondary to various ocular diseases. See, e.g., Kappelhoff, J. P., et al., "The Pathology of After-Cataract. A Mini Review," *Acta Opthamol.* Suppl. 205:13 (1992). For purposes of the present patent application, however, the term secondary cataract means the proliferation, based on histological observations, of lenticular epithelial cells, fibroblasts, macrophages and even iris-derived pigment cells on the posterior capsule following cataract removal, but not the result of unrelated changes in the remaining posterior capsule itself.

Although implanted intraocular lenses themselves are thought to inhibit capsule opacification, the mechanisms by which this results are poorly understood. It has been suggested that intraocular lenses influence secondary cataract formation by limiting the space available for lentoid formation and by maintaining a linear scaffolding for lens epithelial fibrous metaplasia. Nasisse, M. P. et al., "Lens Capsule Opacification in Aphakic and Pseudophakic Eyes," *Graefes Arch. Clin. Exp. Opthalmol.* 233(2):63 (1995). Other commentators have suggested that intraocular lenses stimulate the development of secondary cataract. Nishi, O. et al., "Intercapsular Cataract Surgery with Lens Epithelial Cell Removal," *J. Cataract Refract. Surg.* 17:471–477 (1991). Nonetheless, secondary cataracts occur frequently and require medical intervention.

Various techniques for reducing the opacification of secondary cataracts include, e.g., atraumatic surgery and cortical clean-up. A review of these and other techniques is presented in Apple, D. J. et al., "Posterior Capsule Opacification," *Survey of Ophthalmology*, 37(2):73(1992). These "conventional" treatments for secondary cataracts themselves have serious side effects, including retinal detachment and damage to the implanted intraocular lens. See, e.g, Lundgren, B., et al., "Secondary Cataract: An In vivo Model for Studies on Secondary Cataract in Rabbits," *Acta Opthalmol.* Suppl. 205:25 (1992). Thus, the technique selected for prevention of the formation of secondary cataracts is of particular importance in regard to a successful outcome of the original cataract surgery.

A variety of experimental techniques thus have been proposed or evaluated for the prevention of secondary cataracts. These include the use of heparin to inhibit migration and proliferation of fibroblasts on the posterior capsular surface. Xia, X. P., et al. "A Cytological Study of Inhibition of Secondary Cataract with Heparin," *Chung Hua Yen Ko Tsa Chih*, 30(5):363 (1994); and Xia, X. P., et al. "A Clinical Study of Inhibition of Secondary Cataract with Heparin," *Chung Hua Yen Ko Tsa Chih*, 30(6):405 (1994).

Other approaches to the prevention of secondary cataracts include the chemical modification of the posterior surface of the lens capsule through the covalent binding of certain compounds and their subsequent polymerization. Lindquist, B., et al., "Method for Preventing Secondary Cataract," U.S. Pat. No. 5,375,611 (1994). An alternative approach relates to the injection of a cell-killing substance between the anterior capsule and the natural lens prior to removing the natural lens from the eye. Such a cell-killing substance preferably is a relatively strong acid or base adjusted aqueous solution and may include a viscoelastic material or a dye. Dubroff, S., "Composition for Preventing Clouding of Posterior Capsule After Extracapsular Cataract Eye Surgery and Method of Performing Cataract Surgery," U.S. Pat. No. 5,273,751 (1993).

Somewhat related are chemical methods to prevent or reverse cataract formation involving the administration of chemical compositions that lower the phase separation temperature of a lens and prevent or inhibit the formation of opacities, high molecular weight aggregates and other physical characteristics of cataracts. See, e.g., Clark, J. I., et al., "Chemical Prevention or Reversal of Cataract by Phase Separation Inhibitors," U.S. Pat. No. 5,401,880 (1995).

The use of monoclonal antibodies in the prevention of secondary cataracts also has been reported. For example, complement fixing monoclonal antibodies specific for lens epithelial cells can be introduced into the anterior chamber of the eye following extracapsular extraction. Following the binding of such monoclonal antibodies to any lens epithelial cells present, complement is introduced into the anterior chamber thereby effecting lysis of the remnant lens epithelial cells. Emery, J. M., et al., "Monoclonal Antibodies Against Lens Epithelial Cells and Methods for Preventing Proliferation of Remnant Lens Epithelial Cells After Extracapsular Extraction," U.S. Pat. No. 5,202,252 (1993).

The application of electrical or thermal energy via a probe inserted between the iris and lens capsule also has been used to destroy residual lens epithelial cells within the lens capsule. Bretton, R. H., "Method and Apparatus for Preventing Posterior Capsular Opacification," U.S. Pat. No. 5,455,637 (1995).

Photodynamic therapy for the control of lens epithelial proliferation also has been described. In photodynamic therapy, the photosensitizers used are capable of localizing in target cells, either by natural tendency or because they have been intentionally targeted to a specific type of tissue, or both. When irradiated, they may be capable of fluorescing and, thus, may be useful in diagnostic methods related to detecting target tissue. However, even more importantly, the photosensitizer has the capacity, when irradiated with light at a wavelength which the compound absorbs, of causing a cytotoxic effect against the cells in which the photosensitizer has localized. Although not yet definitively established, it is thought that this cytotoxic effect is due to the formation of singlet oxygen upon irradiation.

With respect to PDT therapy for secondary cataracts, experimental studies using Photofrin II (PII) have been reported by Parel, J. M. et al., "Endocapsular Lavage with Photofrin II as a Photodynamic Therapy for Lens Epithelial Proliferation," *Lasers and Medical Science* 5:25 (1990). These authors noted several technical difficulties with their technique, including a constant leakage of PII from the capsular bag and a minimum uptake time of less than 15 minutes after rinsing. The fluorescence from PII was still discernible after 30 hours, but provided insufficient specificity to guarantee safe photodynamic therapy treatment.

A related study by Lingua, R. et al., "Preclinical Evaluation of Photodynamic Therapy to Inhibit Lens Epithelial Proliferation," *Lasers and Light in Ophthalmology* 2(2):103 (1988) reported the earlier testing of photodynamic therapy using Photofrin II. These authors reported that their techniques did result in local epithelial cell death but also in fiber cell death and that efflux of these agents from the capsule resulted in local ocular toxicities such as uveitis and corneal edema. They suggested that effective inhibition of lens cell proliferation would require capsular containment of the photoactive agent and a method for uniform light delivery within the capsule during photoirradiation. One application of compound included its mixing with Healon® in order to increase the preparation's viscosity.

In another reported study, aluminum phthalocyanine was applied in vitro to preconfluent cultures of porcine lens epithelial cells. Following uptake for one hour, the cultures were exposed to red light for five minutes, and a toxic effect was found. Wunderlich, K. et al., "Photodynamic Activity of Phthalocyanines in Cultivated Lens Epithelial Cells of the Pig," *Ophthalmology* 92(3):346 (1995).

As a related practical constraint, surgeons have expressed concern that even a ten minute delay for uptake of photosensitizers is too long in cataract procedures. Thus, speed of uptake and fairly localized administration of photosensitizer compositions are of particular importance. The prior art compositions do not present such optimal uptake parameters.

According to the present invention, an alternative PDT technique has been developed that uses a preferred group of photosensitizers that are rapidly taken up by remnant lens epithelial cells and that can be contained within the capsule and delivered to target cells during relatively short periods of incubation. The containment of the photosensitizer in the capsule prevents photosensitization of the nontarget parts of the eye. Because these photosensitizers appear green in color rather than red, they have been nicknamed "green porphyrins." These compounds have made it possible to conduct photodynamic therapy with light having a wavelength range outside of that normally strongly absorbed by the blood or other normal tissues, specifically around 670–780 nm. In addition to providing an effective in vivo treatment contained at the target and thereby reducing hypersensitivity of nontarget tissues, an appropriate depth of penetration by the irradiating light may also readily be achieved.

It is known that green porphyrins can be used to detect and treat atherosclerotic plaques in a photodynamic therapy protocol. See, for example, Levy et al., U.S. Pat. No. 5,399,583 issued Mar. 21, 1995 (column 2, lines 14–15); Levy et al., U.S. Pat. No. 4,920,143 issued Apr. 24, 1990 (column 10, lines 58–59); Levy et al., U.S. Pat. No. 5,095,030 issued Mar. 10, 1992 (column 2, lines 8–9 and column 15, lines 29–30); and Levy et al., U.S. Pat. No. 5,171,749 issued Dec. 15, 1992 (column 2, lines 12–13 and column 18, lines 1–4 and 35–47).

A particular class of green porphyrins of some clinical interest is the class of compounds called benzoporphyrin derivatives (BPD). These photosensitizers have been tested to some extent in connection with other ocular conditions. For example, Schmidt, U. et al. described experiments using BPD for the treatment of Greene melanoma (a nonpigmented tumor) implanted into rabbit eyes and achieved necrosis in this context (IOVS 33:1253 Abstract 2802 (1992)). Lin, C. P. et al. describe the measurement of kinetics and distribution in retinal and choroidal vessels by fluorescence imaging using a 458 nm line from an argon-ion laser to excite BPD (IOVS 34:1168 Abstract 2293 (1993)). In addition, Lin, S. C. et al. described photodynamic closure of choroidal vessels using BPD in IOVS 34:1303 Abstract 2953 (1993).

Investigators associated with the assignee of this application have described treating choroidal neovascularization using BPD in several abstracts published Mar. 15, 1993 and in their patent application U.S. Ser. No. 08/390,591) incorporated herein by reference. These abstracts include Schmidt-Erfurth, U. et al. "Photothrombosis of Ocular Neovascularization Using BPD"; Haimovici, R. et al. "Localization of Benzoporphyrin Derivative Monoacid in the Rabbit Eye"; and Walsh, A. W. et al. "Photodynamic Therapy of Experimental Choroidal Neovascularization Using BPD-MA." All of the foregoing are published in IOVS 34:1303 as Abstracts 256, 255 and 254 (1993) and Moulton, R. S. et al. "Response of Retinal and Choroidal Vessels to Photodynamic Therapy Using Benzoporphyrin Derivative Monoacid", IOVS 34:1169 Abstract 58 (1993).

The formulations and PDT methods involving the green porphyrins according to the present invention offer advantages in their selectivity for the cells that give rise to secondary cataracts and in their ability to effect photodynamically mediated destruction of such cells. The green porphyrins also exhibit a relatively faster uptake by target cells, thereby decreasing the delay during operative procedures associated with current PDT techniques. As applied to prevention of secondary cataracts, these kinds of green porphyrins therefore also have particularly advantageous properties in terms of selectivity and rapidity of uptake.

SUMMARY OF THE INVENTION

The invention is directed to the use of photodynamic therapy (PDT) to prevent secondary cataracts using photodynamic methods, primarily employing green porphyrins as the photoactive compounds. These materials offer advantages of rapid uptake by lens epithelial cells, selectivity and effectiveness when employed in protocols directed to the destruction of remnant lens epithelial cells.

Accordingly, in one aspect, the invention is directed to a method to prevent secondary cataracts, which method comprises administering to a subject in need of such treatment an amount of a green porphyrin that will be localized in the lens epithelial cells that give rise to a secondary cataract; and irradiating the cells with light absorbed by the green porphyrin.

In one particular aspect, the invention is directed to a method to prevent secondary cataract in the eye of a subject, which involves the steps of administering to the lens capsule of a subject an amount of a green porphyrin sufficient to permit an effective amount to localize in lens epithelial cells;

permitting a sufficient time to elapse to allow an effective amount of said green porphyrin to localize in lens epithelial cells; and irradiating said lens epithelial cells with light absorbed by the green porphyrin at an energy level sufficient to destroy substantially all of said lens epithelial cells. Specifically, the method involves the destruction of lens epithelial cells that remain following removal of the lens during cataract surgery.

In other aspect, the invention includes a step in which a viscous solution is applied to protect the cornea prior to administration of the green porphyrin. Also, the green porphyrin may be combined with a viscosity-increasing agent. Such viscosity-increasing agents optionally may be selected from the group consisting of hyaluronic acid and its derivatives, starches and cellulose and its derivatives.

In a specific formulation, the inventive methods include the administration of an effective amount of a green porphyrin in the range of about 0.2 to about 2 mg/ml and about 150 to about 250 μl. More specifically, the administered dose is in the range of about 0.03 to about 0.5 mg, and even more specifically, about 0.3 mg. These formulations also may be administered in a liposomal formulation, in which the green porphyrin may be formulated in liposomes before the liposomes are mixed with a viscous vehicle such as Ophthalin, Hymacel or AMVISC.

The methods of the present invention specifically are contemplated for the administration of green porphyrin is selected from the group consisting of BPD-DA, BPD-DB, BPD-MA and BPD-MB as well as the derivatives of these compounds. Particularly preferred BPDs include BPD-MA and BPD-DA.

In a composition aspect, the present invention contemplates pharmaceutical compositions to prevent or inhibit the development of secondary cataracts, such compositions containing an amount of a green porphyrin effective to prevent or inhibit development of the secondary cataract when administered to a subject undergoing cataract surgery; and a pharmaceutically acceptable carrier or excipient.

BRIEF DESCRIPTION OF THE DRAWINGS

The present invention will be more clearly understood by referring to the following drawings, in which:

FIG. 10 shows rabbit epithelial cells treated with BPD and red light. FIG. 10 A is the dark control and FIG. 10B shows light exposed cells.

FIG. 11 shows Vero cells treated with BPD and red light.

DETAILED DESCRIPTION OF THE INVENTION

The present invention is directed to a procedure in which photodynamic therapy (PDT) targets certain cells, i.e., lens epithelial cells, that give rise to secondary cataract at some point in time (perhaps months to years) after cataract surgery. For the prevention of secondary cataract, this treatment is contemplated as an additional procedure during conventional cataract surgery. Thus, following removal of the lens and before insertion, e.g., of a replacement intraocular lens, the normal cataract surgical procedure will be interrupted. An appropriate porphyrin compound, preferably a green porphyrin, will be introduced into the capsule for about one minute and then removed. During that time period, the porphyrin compound will localize in the lens epithelial cells. Light of appropriate frequency and intensity will be applied using an appropriate light source, thereby activating the porphyrin and killing the epithelial cells. Following this PDT procedure, the normal surgical procedure will be resumed and completed.

Figure 1:
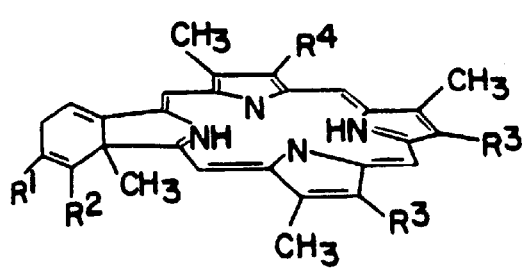
FIG. 1 shows the formulas of typical green porphyrins useful in the method and composition of the invention.
Figure 1:
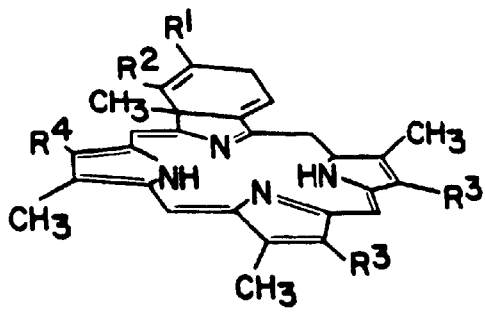
Figure 1:
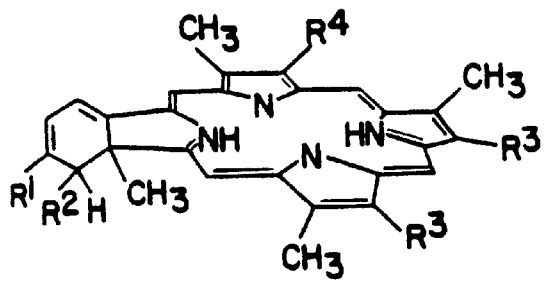
Figure 1:
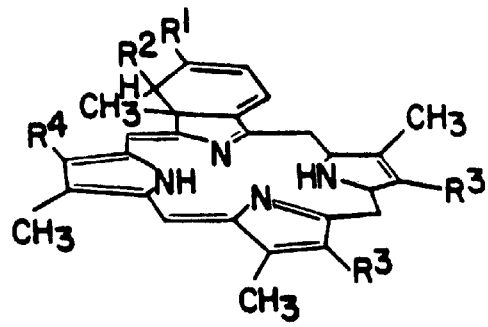
Figure 1:
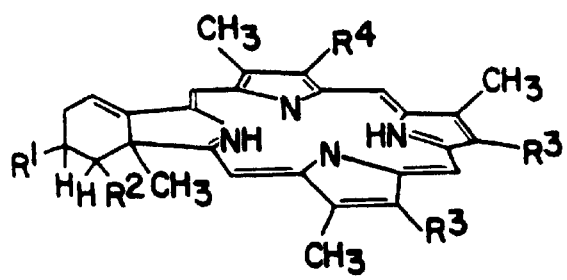
Figure 1:
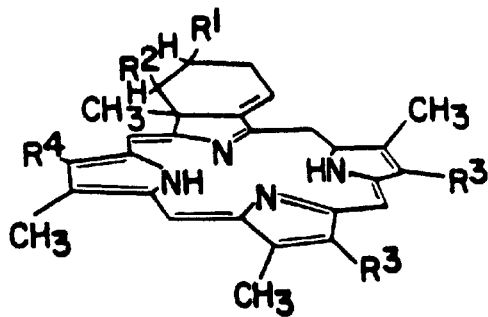

The formulations and methods of the claimed invention generally relate to administering to a subject a green porphyrin, which is in the class of compounds called benzoporphyrin derivatives (BPD). A BPD is a synthetic chlorin-like porphyrin with various structural analogues, as shown in FIG. 1. Preferably, the green porphyrin is benzoporphyrin derivative di-acid or mono-acid ring A (BPD-DA or BPD-MA), which absorbs light at about 692 nm wavelength with improved tissue penetration properties. BPD-MA, for example, is lipophilic, a potent photosensitizer, and it also appears to be phototoxic to neovascular tissues, tumors and remnant lens epithelial cells. After about a less than one minute period for uptake of an appropriate formulation of, e.g., a BPD-MA composition by lens epithelial cells, light of the appropriate wave length is delivered substantially uniformly to all lens epithelial cells located on the inner anterior and equatorial surfaces of the capsule. Because of its pharmokinetics, BPD appeared to be the best candidate for use in this indication, but other green porphyrins such as BPD-DA or other derivatives (see Formulas 1–6 in FIG. 1) may be used instead. Other photosensitizers, such as phthalocyanines, could be used in high concentrations sufficient to offset their relatively slower uptake. However, with such compounds, the skilled artisan would need to formulate any sensitizer selected so as to control the possibility of inadvertant comtamination of other parts of the eye.

A particularly preferred formulation according to the present invention will satisfy the following general criteria. First, a photosensitizer capable of rapid entry into the target lens epithelial cells must be utilized. Second, the viscosity of the product must ensure that it is substantially contained within the capsule during the incubation period. Third, components that facilitate the uptake of this photosensitizer by the target cells may be included. As an example of a specific formulation, 0.1 ml of BPD-MA stock solution is added to 1.9 ml of a viscoelastic such as Ophthalin and mixed according to the examples that follow.

During cataract surgery, the anterior wall of the lens is either cut, to facilitate the extracapsular lens extraction, or partly removed (capsulorhesis) to facilitate the introduction of a phacoemulsifier to carry out the intercapsular lens extraction. Accordingly, the successful containment of a photosensitizer in the capsule for the indicated incubation period will depend on the viscosity of the formulation in which the photosensitizer is introduced into the capsule. The time of such incubation also is significant in containment and preferably will be for less than about one minute, ideally less than about 45 seconds and most preferably less than about 30 seconds, The cut in the interior surface of the capsule and administration of the PDT compound may result in spillage of the photosensitizer administered to prevent secondary cataracts and may limit its, retention at the intended intracapsular site. Thus, an additional important aspect of the present invention is the coating of the corneal endothelium with drug-free viscoelastic material before applying the photosensitizer, in order to protect this sensitive part of the eye from contamination with the photosensitizer.

Other considerations also should be taken into account when administering PDT to prevent secondary cataract. For example, the shape of the capsule, i e., an elongated sphere, with cells having high mitotic potential in the equatorial position, and its small size make uniform light delivery difficult when photodynamic therapy is contemplated. As an additional constraint, the busy operative schedules of eye surgeons do not allow time for a lengthy procedure to be added to the cataract procedure itself. Accordingly, an optimal photosensitizer for PDT prevention of secondary cataracts must be rapidly taken up by lens epithelial cells and should be physically contained, to a significant extent, within the capsule.

After the photosensitizing green porphyrin has been administered, preferably the compound is allowed to be taken up by lens epithelial cells for less than about one minute. The lens epithelial cells then are irradiated at the wavelength of maximum absorbence of the green porphyrin, usually between about 550 and 695 nm, as discussed above. In particular, red light is advantageous because of its relatively lower energy and the resulting lack of toxicity it poses to ocular tissue while the lens epithelial cells are destroyed.

The compositions and methods of the present invention provide a useful PDT treatment to prevent secondary cataracts. The following describes the compositions and formulations of the present invention and their clinical application. Experimental data also are presented and described.

The Green Porphyrins:

The green porphyrins useful in the method of the invention are described in detail in Levy et al., U.S. Pat. No. 5,171,749 issued Dec. 15, 1992, which is incorporated herein by reference. "Green porphyrins" refer to porphyrin derivatives obtained by reacting a porphyrin nucleus with an alkyne in a Diels-Alder type reaction to obtain a monohydrobenzoporphyrin. Typically, green porphyrins are selected from a group of porphyrin derivatives obtained by Diels-Alder reactions of acetylene derivatives with protoporphyrin under conditions that promote reaction at only one of the two available conjugated, nonaromatic diene structures present in the protoporphyrin-IX ring system (rings A and B).

Several structures of typical green porphyrins are shown in FIG. 1. The Diels-Alder reaction initially results in the formation of a cyclohexadiene—referred to herein as "hydrobenzo"—fused to the A or B pyrrolic ring, as shown in formulas 1 and 2. Rearrangement of the π system in the hexadiene ring results in the formation of compounds of formulas 3 and 4, and reduction provides compounds of formulas 5 and 6. These compounds are shown in formulas 1–6 with hydrogen occupying the internal ring nitrogens. However, it is to be understood that the methylated forms, in which a cation replaces one or both of these hydrogens, can also be used. The preparation of the green porphyrin compounds useful in this invention is described in detail in U.S. Pat. No. 5,095,030, which is incorporated herein by reference.

For convenience, an abbreviation of the term hydromonobenzoporphyrin derivativegroups—"BPD"—is generally used to refer to compounds of formulas 3 and 4 of FIG. 1. Compounds of the formulas 3 and 4 and mixtures thereof are particularly preferred.

As shown in FIG. 1, $R^1$, $R^2$, $R^3$ and $R^4$ are noninterfering substituents that do not appreciably affect the activity of the compound in the method and composition of the invention. More specifically, the term "noninterfering substituents" is used to mean substituents that do not interfere with BPD's pharmacological functions. For the compounds of FIGS. 1 and 2, generally, $R^1$ and $R^2$ are each, independently, moderately electron-withdrawing substituents or any other activating substituents that are not sufficiently electron-withdrawing to result in the Diels-Alder reaction proceeding with both A and B rings, rather than only one. Examples of suitable $R^1$ and $R^2$ groups include carbalkoxy (2–6C), alkyl (1–6C) sulfonyl or aryl (6–10C) sulfonyl, aryl (6–10C), cyano, and —$CONR^5CO$— where $R^5$ is aryl (6–10 C) or alkyl (1–6). One of $R^1$ and $R^2$ may also be hydrogen, so long as the other is an electron-withdrawing substituent of sufficient strength to facilitate the Diels-Alder reaction. Most commonly, $R^1$ and $R^2$ are carbalkoxy groups, preferably methyl or ethyl carboxy esters. Preferred compounds are those in which $R^1$ and $R^2$ are the same and are carbalkoxy, particularly carboethoxy.

As used herein, the term "carboxy" is, as conventionally defined, —COOH, while "carbalkoxy" represents —COOR where R is alkyl. "Carboxyalkyl" refers to the substituent —R'—COOH where R' is alkylene. "Carbalkoxyalkyl" refers to —R'—COOR where R' and R are alkylene and alkyl respectively. "Alkyl" generally represents a saturated straight or branched chain hydrocarbyl moiety of 1–6 carbon atoms, such as methyl, n-hexyl, 2-methylpentyl, t-butyl, n-propyl, and so forth. "Alkylene" is the same as "alkyl" except that the group is divalent rather than monovalent. "Aryl" represents a phenyl group, optionally substituted with 1–3 substituents, which may be independently selected from the group consisting of halo, such as fluoro, chloro, bromo or iodo; lower alkyl (1–4C); and lower alkoxy (1–4C). "Aryl" or "alkyl sulfonyl" groups have the formula —$SO_2R$ where R is alkyl or aryl as defined above.

$R^3$ is independently a ω-carboxyalkyl group (2–6C) or a salt, amide, ester or acylhydrazone thereof, or is alkyl (1–6C). Preferably, $R^3$ is 2-carboxyethyl or the alkyl ester thereof, and $R^4$ is vinyl. These embodiments, however, are preferred because of the availability of native porphyrins, rather than being mandated by considerations of biological efficacy. As shown in FIG. 1, adducts formed by the reaction of $R^1$—C≡C—$R^2$ with a protoporphyrin-IX ring system (where $R^3$ is a protected form of 2-carboxyethyl, such as 2-carbomethoxyethyl or 2-carboethoxyethyl, and $R^4$ is —CH=$CH_2$) are compounds of the formulas 1 and 2. Compounds of formula 1 result from the addition to the A ring, and compounds of formula 2 result from the addition to the B ring.

Convenient starting materials for the green porphyrin compounds of the invention include the naturally-occurring porphyrins where $R^3$ is either —$CH_2CH_2COOH$ or —$CH_2CHRCOOR$ where R is alkyl (1–6C). However, the exact nature of $R^3$, unless it contains a π-bond conjugated to ring π-bond, is ordinarily not relevant to the progress of the Diels-Alder reaction or to the effectiveness of the resulting product. $R^3$ can thus be any one of a wide variety of groups such as, for example, lower alkyl (1–4C); and ω-carboxyalkyl (2–6C) and the esters and amides thereof. The $R^3$ substituent may also be substituted with halogen, such as fluoro, chloro, bromo or iodo; or with other nonreactive substituents.

When $R^3$ is $CH_2CHRCOOR$, it has been found advantageous to hydrolyze, or partially hydrolyze, the esterified carboxy group. Typically, the hydrolysis at the $R^3$-position conveniently occurs at a much faster rate than that of the ester groups of $R^1$ or $R^2$. Further, the solubility and biodistribution characteristics of the resulting compounds are more desirable than those of the unhydrolyzed form. Hydrolysis results in the diacid or monoacid products (or their salts).

In compounds of formulas 1 and 2, $R^4$ is usually —CH=$CH_2$, at least initially, but this vinyl group is readily derivatized to other embodiments of $R^4$ by the addition to, or oxidation of, the vinyl ring substituent of ring B or A in formula 1 or 2 respectively. Thus, $R^4$ can be any one of a wide variety of substituents that are consistent with that formed by a facile addition reaction. For example, an exemplary addition reagent may be of the form HX where H is added to the carbon adjacent to the ring to provide an $R^4$-position having the formula:

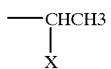

Thus, in one embodiment, one of the added substituents is a hydrogen, and the other one is selected from the group consisting of hydrogen; halo such as fluoro, chloro, bromo or iodo; hydroxy; lower alkoxy; amino; amide; sulfhydryl; or an organosulfide. For example, the Markovnikov addition of water provides a substituent structure analogous to a hematoporphyrin ring system at the relevant ring. The vinyl group can also be oxidized to obtain, as a substituent in the $R^4$-position, —$CH_2OH$, —CHO, or COOH or its salts or esters. The addition or oxidation products can themselves also be substituted if the added substituents are functional leaving groups. For example, when Br is a substituent, it may be replaced by such moieties as —OH, —OR where R is alkyl (1–6C) as described above, halo, —$NH_2$, —NHR, —$NR_2$ and the like. Thus, in general, $R^4$ represents any substituents to which the vinyl group —CH=$CH_2$ is readily converted by cleavage or addition, and further substituents formed by the reaction of leaving good groups with additional moieties. Preferably, however, $R^4$ is vinyl (—CH=$CH_2$); —$CHOR^{4'}$ where $R^{4'}$ is H or alkyl (1–6C), optionally substituted with a hydrophilic substituent such as —$CH_2OH$; —CHO; —$COOR^{4'}$ such as COOH or —$COOCH_3$; —$CH(OR^{4'})CH_3$ such as —$CH(OH)CH_3$ or —$CH(OCH_3)CH_3$; —$CH(OR^{4'})CH_2OR^{4'}$; —$CH(OH)CH_2OH$; —$CH(SR^{4'})CH_3$ such as —$CH(SCH_3)CH_3$ and the disulfide thereof; —$CH(NR^{4'})CH_3$; —$CH(CN)CH_3$; —CH(pyridinium bromide)$CH_3$; —$CH(COOR^{4'})CH_3$; —CH($COOCR^{4'})CH_3$; —$CH_2$(halo)$CH_3$ such as —$CHBrCH_3$; or —$CH(halo)CH_2$(halo). Alternatively, $R^4$ can be an organic group of less than 12 carbon atoms resulting from the direct or indirect derivatization of vinyl. Or $R^4$ can provide additional porphyrin or porphyrin-related ring systems, such as a group containing from 1–3 tetrapyrrole-type nuclei of the formula —L—P, as defined below. Those compounds in which $R^4$ is —CH=$CH_2$, —$CH(OH)CH_3$, —$CH(halo)CH_3$, or a group containing 1–3 tetrapyrrole-type nuclei of the formula —L—P, as defined below, are preferred.

As used herein, the term "tetrapyrrole-type nucleus" represents a four-ring system of the skeleton:

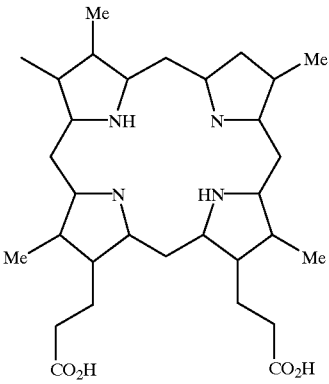

or a salt, ester, amide, or acylhydrazone thereof, which is highly conjugated. It includes the porphyrin system, which is in effect a completely conjugated system; the chlorin system, which is in effect a dihydro form of the porphyrin; and the reduced chlorin system, which is a tetrahydro form of the conjugated porphyrin system. When "porphyrin" is specified, the completely conjugated system is indicated. Green porphyrins are effectively a dihydro form of the porphyrin system.

In one embodiment, the substituent $R^4$ includes at least one additional tetrapyrrole-type nucleus. The resulting compounds of the invention are dimers or oligomers in which at least one of the tetrapyrrole-type ring systems is a green porphyrin. Linkage between the green porphyrin moiety at the $R^4$-position to an additional tetrapyrrole-type ring system may be by an ether, amine or vinyl linkage. Porphyrin ring systems having two available substituent positions (in both A and B rings) corresponding to $R^4$ can be additionally derivatized, as explained below.

When R4 is "—L—P," —L— is selected from the group consisting of:

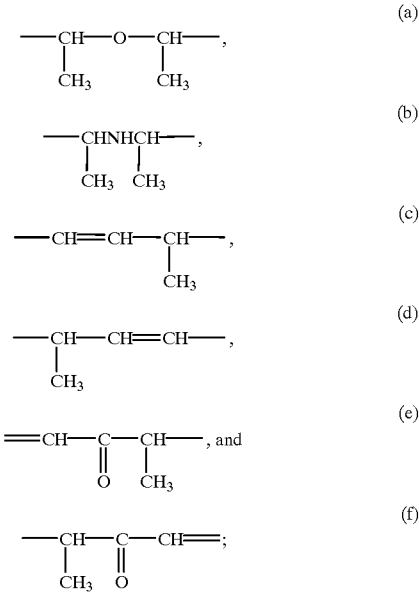

and P is a porphyrin structure or a second green porphyrin of the formulas 1–6 shown in FIG. 1, except that any second R4 group is replaced by L above.

(It is also understood that, when —L— is of the formula (e) or (f) shown above, the ring system to which the double bond is attached will have a resonance system corresponding to

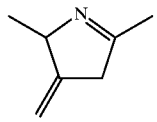

in the ring to which the double bond is attached, as shown.)

The hydromonobenzoporphyrins that directly result from the Diels-Alder reaction described above can also be isomerized to the BPD compounds of formulas 3 and 4 of FIG. 1. The depictions of compounds 3 and 4 in FIG. 1 do not show the relative position of the exocyclic methyl group (ring A of formula 3 and ring B of formula 4) with respect to the $R^2$ substituent. Either isomer is available. Compounds of formulas 3 and 4 are particularly preferred in the methods and compositions of the invention.

In addition, the Diels-Alder products can be selectively reduced by treating with hydrogen in the presence of a catalyst, such as palladium on charcoal, to give the saturated ring analogs, shown as formulas 5 and 6 in FIG. 1, which correspond to the respective Diels-Alder products of rings A and B. The description set forth above with respect to the compounds of formulas 1 and 2 concerning derivatization by conversion of the remaining vinyl substituent ($R^4$) and with respect to the variability of $R^3$ applies as well to the compounds of formulas 3, 4, 5 and 6.

Preferred embodiments of the green porphyrins of the invention are those in which the Diels-Alder product is rearranged and partially hydrolyzed. Even more preferred are the compounds of formulas 3 and 4 (BPDs) in which the carbalkoxy groups in the $R^3$-positions have also been hydrolyzed or partially hydrolyzed. Compounds of the invention that contain —COOH may be prepared as either the free acid or in the form of salts with organic or inorganic bases.

Figure 2:
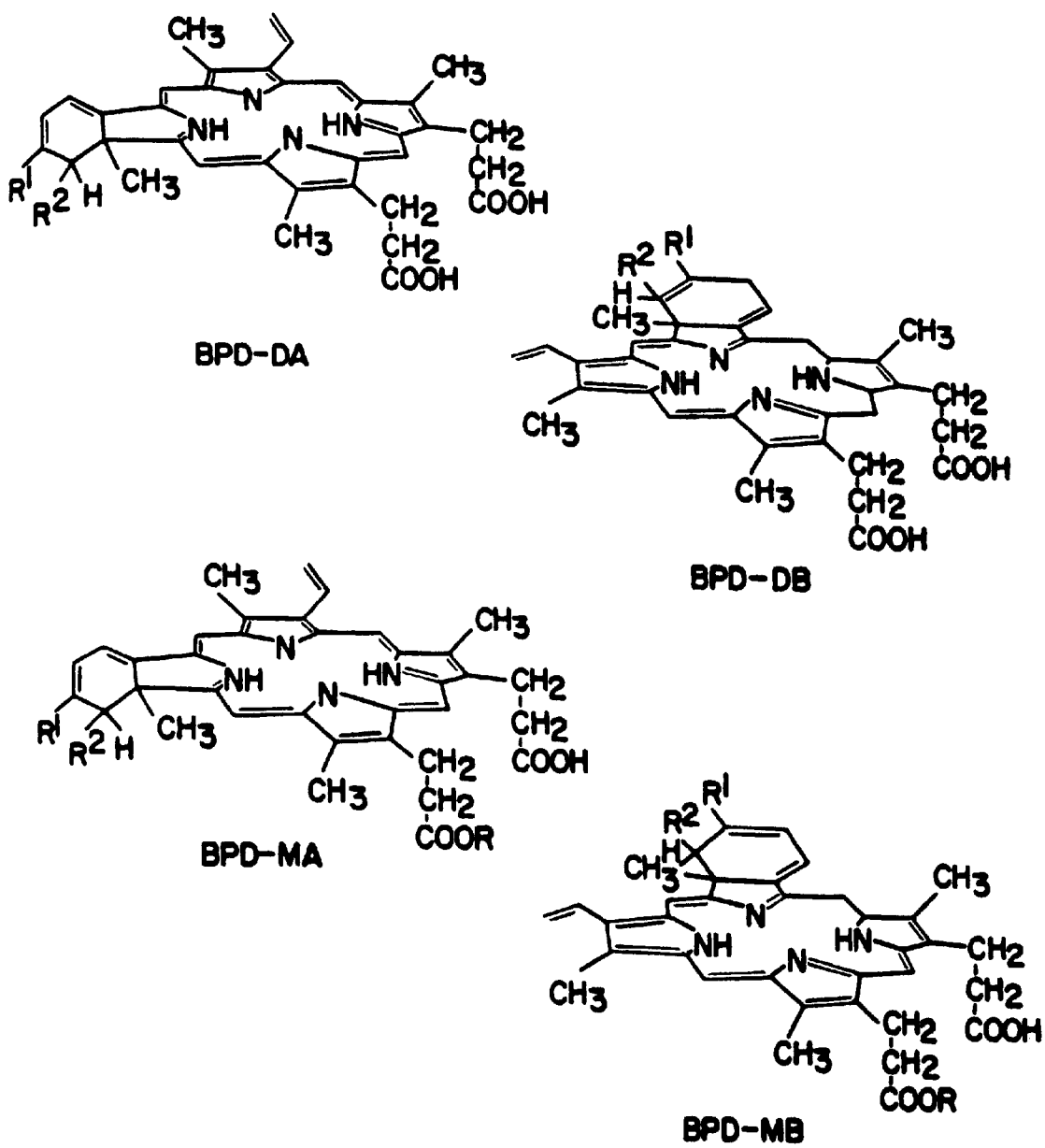
FIG. 2 shows the formulas of four particularly preferred embodiments of the green porphyrins of the invention, BPD-DA, BPD-DB, BPD-MA and BPD-MB.

FIG. 2 shows four particularly preferred compounds of the invention covered by formulas 3 and 4, which are collectively designated as benzoporphyrin derivatives, i.e., BPD-DA, BPD-DB, BPD-MA and BPD-MB. These are hydrolyzed or partially hydrolyzed forms of the rearranged products of formula 3 and 4, wherein one or both of the protected carboxyl groups of $R^3$ have been hydrolyzed. The ester groups at $R^1$ and $R^2$ hydrolyze relatively slowly, so that conversion to the forms shown in FIG. 2 is easily effected. The most preferred of these green porphyrin compounds is BPD-MA.

In FIG. 2, $R^3$ is —$CH_2CH_2COOR^{3'}$ where $R^{3'}$ varies by individual compound. Specifically, in BPD-DA, $R^1$ and $R^2$ are carbalkoxy, $R^{3'}$ is hydrogen, and derivatization is at ring A. BPD-DB is the corresponding compound with derivatization at ring B. BPD-MA represents the partially hydrolyzed form of BPD-DA, and BPD-MB represents the partially hydrolyzed form of BPD-DB. Thus, in these latter compounds, $R^1$ and $R^2$ are carbalkoxy, one $R^{3'}$ is hydrogen, and the other $R^{3'}$ is alkyl (1–6C).

The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates. In addition, mixtures of any two or more of BPD-MA, -MB, -DA and -DB may be used in the methods of and compositions of the invention.

It should be noted that many of the compounds of FIG. 1 contain at least one chiral center and, thus, may exist as optical isomers. The method of the invention can use compounds having both configurations of the chiral carbons, whether the compounds are supplied as isolates of a single stereoisomer or are mixtures of enantiomers and/or diastereomers. Separation of mixtures of diastereomers may be effected by any conventional means. Mixtures of enantiomers may be separated by any of the usual techniques, such as by reacting them with optically active preparations and separating the resulting diastereomers.

It should further be noted that the reaction products may be unseparated mixtures of A and B ring additions, e.g., mixtures of formulas 1 and 2 or 3 and 4 or 5 and 6. Either the separated forms, e.g., formula 3 alone or 4 alone, or mixtures in any ratio, may be used in the methods and compositions of the invention.

Further still, dimeric forms of the green porphyrin and dimeric or multimeric forms of green porphyrin/porphyrin combinations can be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

The green porphyrin compounds of the invention may be administered as a single compound, preferably BPD-DA or BPD-MA, or as a mixture of various green porphyrins. Suitable formulations include those appropriate for administration of therapeutic compounds to the eye. Additionally, other components may be incorporated into such formulations. These include, for example, visible dyes or various enzymes to facilitate the access of a photosensitizing compound to target cells across the remnants of lens material.

Green Porphyrin Formulations:

The compositions of the present invention may also comprise further components, such as conventional delivery vehicles and excipients including isotonising agents, pH regulators, solvents, solubilizers, dyes, gelling agents and thickeners and buffers and combinations thereof.

Typically, the photosensitizing agent is formulated by mixing it, at an appropriate temperature, e.g., at ambient temperatures, and at appropriate pHs, and the desired degree of purity, with one or more physiologically acceptable carriers, ie., carriers that are nontoxic at the dosages and concentrations employed. Generally, the pH of the formulation depends mainly on the particular use, and concentration of photosensitizer, but preferably ranges anywhere from about 3 to about 8. Preferably, the photosensitizer is maintained at a pH in the physiological range (e.g., about 6.5 to about 7.5). The presence of salts is not necessary, and, therefore the formulation preferably is not an electrolyte solution. Appropriate nonantigenic ingredients, such as human serum albumin, may optionally be added in amounts that do not interfere with the photosensitizing agent being taken up by lens epithelial cells.

Because the photosensitizing agent formulation is to be applied to the lens capsule during a cataract extraction procedure where leakage is undesirable, it is preferable to use a viscous solution such as a gel, rather than a nonviscous solution. Preferably, the formulation is prepared such that its viscosity is sufficient to contain the photosensitizing drug substantially within a capsule that has been cut open widely. A preferred formulation uses about 5% (v/v) green porphyrin formulated in liposomes and about 95% (v/v) sodium hyaluronate such as Ophthalin.

The foregoing ratio of photosensitizing agent to viscous carrier is preferable, and may be varied depending on the particular viscosity agent and any optional ingredients that are also utilized in the formulation to be administered. Moreover, the same final viscosity can be achieved with a variety of different ingredients such as polysaccharide, preferably a water-soluble polysaccharide, e.g., hyaluronic acid, starches, and cellulose derivatives (such as methylcellulose, hydroxyethyl cellulose, and carboxymethyl cellulose). When a polysaccharide is present in a gel formulation, the amount usually present is in the range of about 1–90% by weight of the gel, more preferably about 1–20%. Examples of other suitable polysaccharides for this purpose and a determination of the solubility of the polysaccharides are found in EP 267,015 published May 11, 1988. Other thickeners may also be added to the formulations of the invention in standard amounts, typically organic cellulose ethers such as hydroxypropyl methyl cellulose, or hyaluronic acid salts such as the sodium salt of hyaluronic acid. Customary buffers can also be added in standard amounts.

The particular concentration of a given green porphyrin should be adjusted according to its photosensitizing potency. For example, BPD-DA can be used but at about a five-fold higher concentration than that of BPD-MA. Moreover, the BPD may be solubilized in a different manner than by formulation in liposomes. For example, stocks of BPD-MA or any other green porphyrin may be diluted in DMSO (dimethylsulfoxide), poyethylene glycol or any other solvent acceptable for use in the eye. Still, the proportion between the volume of the drug and the volume of viscous material should be kept relatively constant, to preserve the viscosity and thus the containability of the drug in the capsule.

Normally, the adjustment of pH is not required when liposomal BPD-MA is used, as both components (i.e., BPD and the viscous material) have a neutral pH. However, when other solvents than liposomes are used, the pH should be adjusted before mixing the drug with the viscous material. Bacteriostatic agents approved for use in the eye optionally may be added to the formulation, but antioxidants may interfere with the treatment and thus generally should be avoided.

Preparation of dry formulations that are reconstituted immediately before use also are contemplated. The preparation of dry or lyophilized formulations of the compositions of the present invention can also be effected in a known manner, conveniently from the solutions of the invention. The dry formulations of this invention are also storable. By conventional techniques, a solution can be evaporated to dryness under mild conditions, especially after the addition of solvents for azeotropic removal of water, typically a mixture of toluene and ethanol. The residue is thereafter conveniently dried, e.g. for some hours in a drying oven.

Suitable isotonising agents are preferably nonionic isotonising agents such as urea, glycerol, sorbitol, mannitol, aminoethanol or propylene glycol. In contrast, ionic isotonising agents such as sodium chloride are generally unsuitable in the context of this invention. The solutions of this invention will contain the isotonising agent, if present, in an amount sufficient to bring about the formation of an approximately isotonic solution. The expression "an approximately isotonic solution" will be taken to mean in this context a solution that has an osmolarity of about 300 milliosmol (mOsm), conveniently 300+10% mOsm. It must be borne in mind that all components of the solution contribute to the Osmolarity. The nonionic isotonising agent, if present, is added in customary amounts, i.e., preferably in amounts of about 1 to about 3.5 percent by weight, preferably in amounts of about 1.5 to 3 percent by weight.

Solubilizers such as Cremophor types, preferably Cremophor RH 40, or Tween types or other customary solubilisers, may be added to the solutions of the invention in standard amounts.

A further preferred embodiment of the invention relates to a solution comprising a green porphyrin compound, and a partially etherified cyclodextrin, the ether substituents of which are hydroxyethyl, hydroxypropyl or dihydroxypropyl groups, a nonionic isotonising agent, a buffer and an optional solvent. However, appropriate cyclodextrins must be of a size and conformation appropriate for use with the photosensitizing agents disclosed herein.

Administration of Green Porphyrin Compound:

As noted above, the treatment of the present invention is carried out between removal of the lens and the introduction of an intraocular lens. It represents a relatively short interlude in typical cataract surgery procedures. Thus, surgery on the eye is performed in accordance with standard procedures until the lens has been extracted. The lens cavity preferably is washed with a physiological balanced salt solution and the green porphyrin composition according to this invention is applied, preferably in a viscous formulation as described above in order to increase retention within the lens capsule and to reduce spillage. The preparations of the present invention preferably are administered through a cannula attached to a reservoir such as a syringe. The solution is allowed to act for about ½ to about 10 minutes, preferably for about 1 to about 3 minutes, more preferably for less than about 1 minute and most preferably for 15 to 30 seconds. After such incubation, the lens cavity preferably is washed once more with the balanced salt solution to remove excess green porphyrin. Appropriate light is applied immediately after the wash.

Using an appropriate light source, preferably a laser or laser diode, in the range of about 550 to about 695 nm, the lens epithelial cells are exposed to light for a period of time sufficient to destroy residual lens epithelial cells. An appropriate and preferred wavelength for such a laser would be 690±12.5 nm at half maximum. Generally, epithelial cell destruction occurs within 60 seconds, and likely is sufficiently complete within about 15 to about 30 seconds. Finally, optionally, the lens capsule is washed once more with an appropriately buffered saline solution, and the cataract operation is completed in accordance with standard procedures by inserting, e.g., an artificial lens. Alternatively, cells within the epithelium of the lens capsule can also be killed by injecting a green porphyrin solution subcapsularly direct into the still intact lens (hydrodissection). Excess compound is washed out together with fragments and thereafter irradiation of the target cells is carried out with an appropriate light source. The overall surgical procedure would be modified appropriately.

In an alternative and preferred embodiment, the green porphyrin is prepared as a liposomal preparation or is coupled to a ligand, such as a monoclonal antibody, that binds to a specific surface component of lens epithelial cells to improve even further its effectiveness as a photosensitizer. Preferably, the ligand comprises an antibody or an immunologically reactive fragment thereof. As noted above, the capacity for selective localization of a green porphyrin can be improved further during eye surgery by being provided in a composition with a higher viscosity than aqueous preparations, thereby reducing leakage or spillage from the capsule during surgical procedure. This approach delivers higher concentrations of the green porphyrin to the target tissue.

The dose of green porphyrin can be optimized by the skilled artisan depending on the physical delivery system in which it is carried, such as in the form of liposomes; or whether it is coupled to a target-specific ligand, such as an antibody or an immunologically active fragment.

It should be noted that the various parameters used for effective, selective photodynamic therapy in the invention are interrelated. Therefore, the dose should also be adjusted with respect to other parameters, for example, fluence, irradiance, duration of the light used in photodynamic therapy, and time interval between administration of the dose and the therapeutic irradiation. All of these parameters should be adjusted to produce significant damage to remnant lens epithelial cells without causing significant damage to the surrounding tissue. Typically, the dose of green porphyrin will be administered by applying less than about 200 microliters in volume of the formulation to the interior lens capsule. More or less of the formulation may be applied depending on the size of the incision made to the lens capsule, the condition of the lens, and the presence or absence of other materials such as blood or wash solutions. Generally, the skilled artisan should attempt to provide a local exposure to a sufficient amount of a green porphyrin compound, and any excess compound will be washed out and in any event does not present a substantial risk of toxicity. The concentration of green porphyrin used generally is within the range of from about 0.2 to about 2.0 mg/ml, preferably from about 0.5 to about 1.5 mg/ml, and even more preferably about 1.0 mg/ml. The foregoing concentrations can be varied by the skilled artisan so that the uptake and cellular destruction parameters are consistent with the therapeutic objectives disclosed above.

As a result of being irradiated, the green porphyrin in its triplet state is thought to interact with oxygen and other compounds to form reactive intermediates, such as singlet oxygen, which can cause disruption of cellular structures. Possible cellular targets include the cell membrane, mitochondria, lysosomal membranes.

The light dose administered during the PDT treatment contemplated herein can vary, but preferably ranges between about 10 to about 150 $J/cm^2$. The range between about 50–100 $J/cm^2$ is preferred. Increasing irradiance may decrease the exposure times.

The time of light irradiation after administration of the green porphyrin may be important as one way of maximizing the selectivity of the treatment, thus minimizing damage to structures other than the target cells and facilitating the conclusion of the surgical procedure. Treatment immediately after application of the photosensitizer should generally be attempted.

EXAMPLE 1

Evaluation of BPD Toxicity in Cultured HLE Cells

In order to assess its overall toxicity, a technique was established for culturing human lens epithelial (HLE) cells, obtained either from donor eyes or from cataract surgeries.

The majority of human lens epithelial (HLE) cells was grown from lenses from 12–48 hr post-mortem donor eyes supplied as posterior poles (corneas previously removed) by the Eye Bank of British Columbia. Occasionally, whole eyes were supplied. Also, excised lenses stored for 1–5 hours in cold PBS were occasionally supplied. Lens capsules were harvested from male and female donors ranging from 20 to 72 years in age. In all cases a circumferential incision was made at the equator (and/or up to 0.5 mm anterior to the equator) in the anterior capsule of the lens. This explanted tissue was placed cell-side down onto a plastic tissue culture dish (35 mm) with DME supplemented with 15% FCS. The capsules were then cut into a series of 1 mm wide parallel strips by using a rocking motion of a rounded scalpel blade which welded the edges of the capsule strips onto the surface of the dish. The explants were fed fresh media every two to three days. Cell outgrowth was allowed to continue until the monolayer was confluent or nearly confluent then passaged with 0.25% trypsin in EDTA. HLE cells were used at either passage two or three. VERO Green Monkey kidney cells (supplied from QLT) were grown in the same media conditions as HLE and used before reaching passage 20 from frozen stocks.

Figure 3:
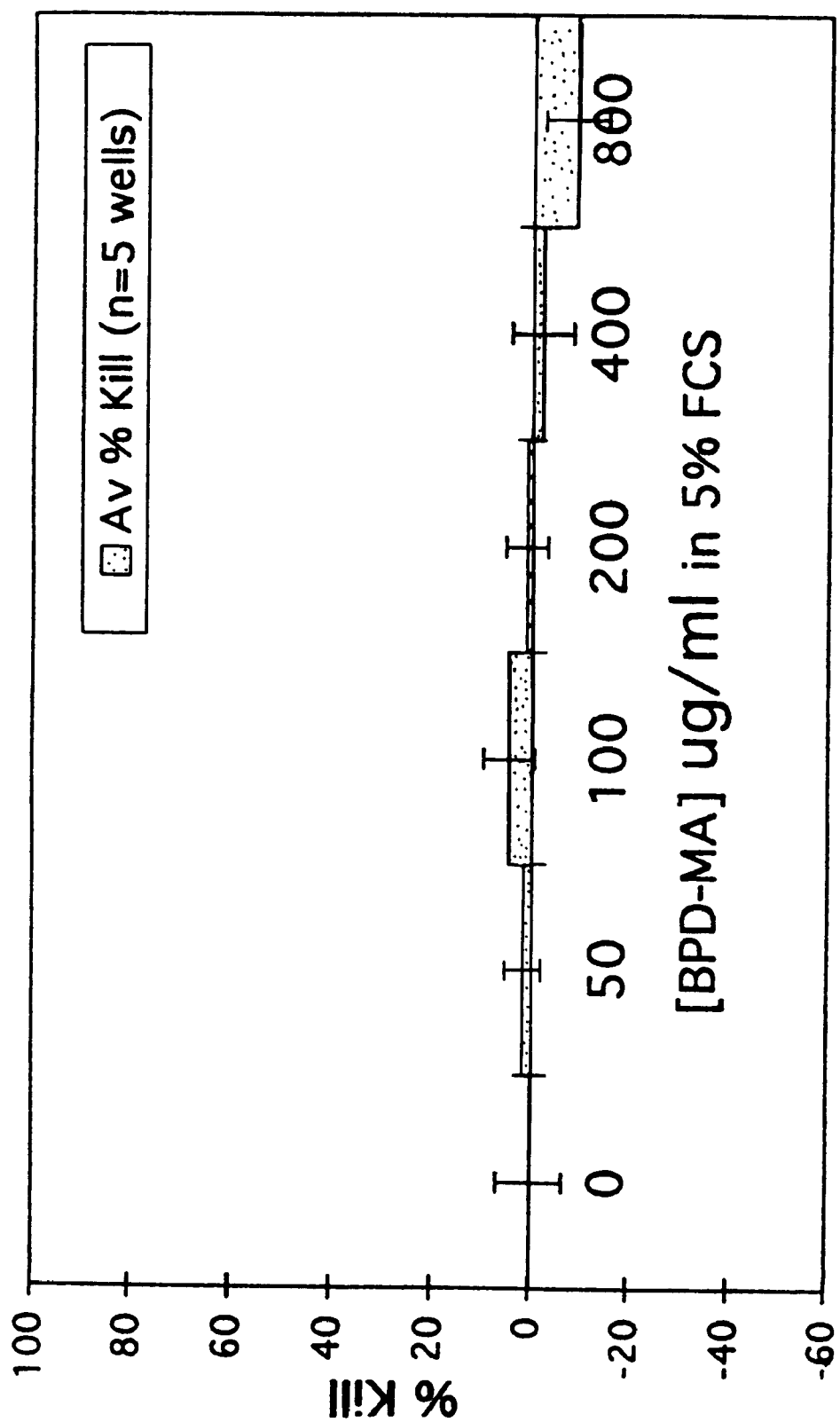
FIG. 3 shows the survival of human lens epithelial cells following incubation with BPD in the absence of light.

In this system, it was determined that a 10 min. incubation with BPD alone (in 5% fetal calf serum, FCS) at a range of concentrations (0–800 µg/ml) does not affect the cell survival (FIG. 3).

EXAMPLE 2

Treatment of HLE Cells with Light Following Incubation with BPD

Figure 4A:
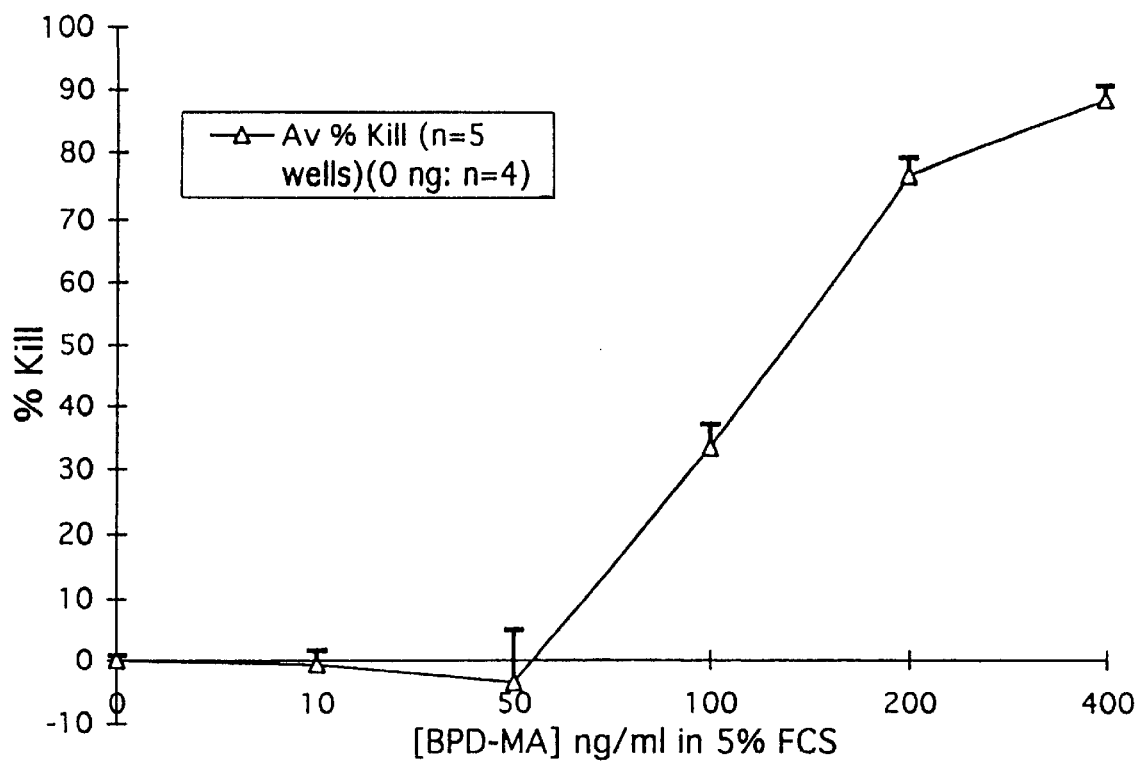
FIG. 4 shows the cytotoxic effect of BPD and light on human lens epithelial cells.
Figure 4B:
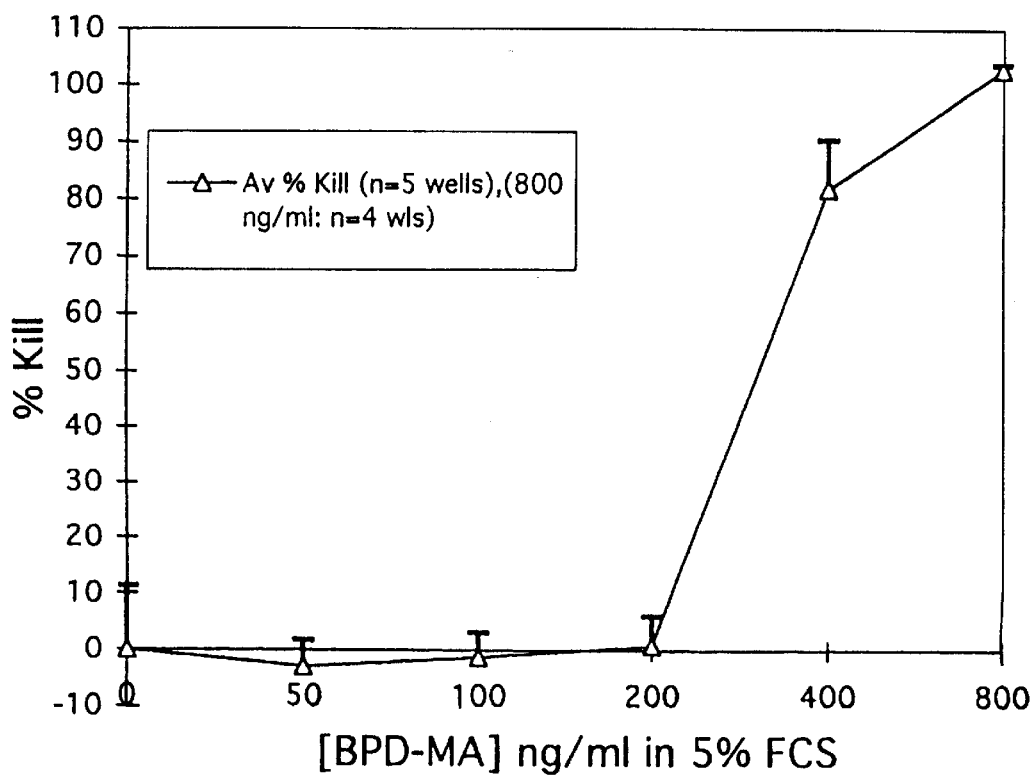
Figure 5A:
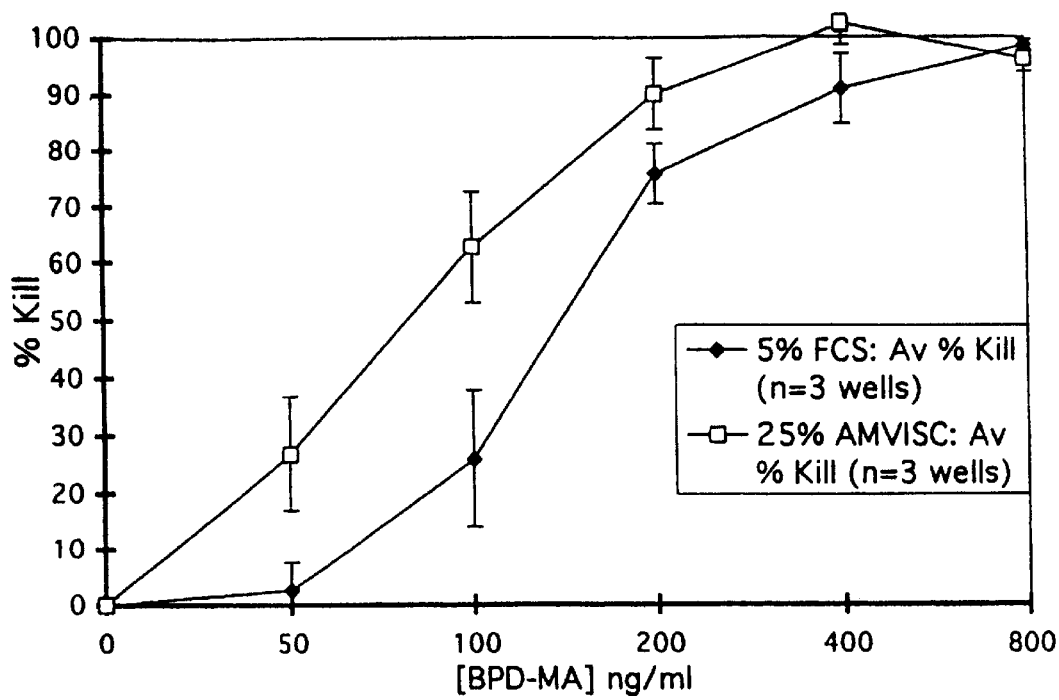
FIG. 5 shows that the cytotoxic effect of PDT are long lasting.
Figure 5B:
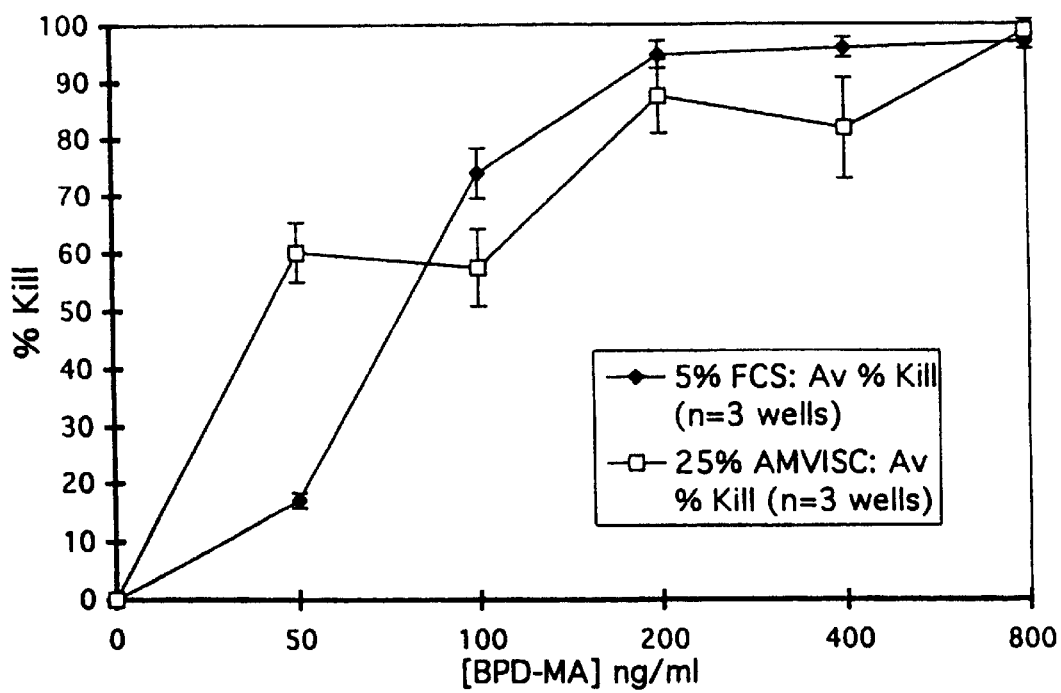

Cells from Example 1 were exposed to 10 $J/cm^2$ of red light (690±12.5 nm) delivered with light emitting diodes (LED), immediately after a 10 min. incubation with BPD but subsequent to removal of excess drug. As anticipated, the cell survival was greatly reduced. In the presence of 5% FCS, 400–800 ng BPD/ml followed by red light resulted in 80–100% cell kill. In related experiments conducted in vitro, the sensitivity of HLE cells to BPD and light differed, depending on donors and number of passages in culture (FIG. 4). Cell survival was determined by means of a colorimetric assay, MTT, which measures both the cells metabolic state and proliferation, and thus reflects both the cytotoxic and cytostatic effects. See, Mossman, "Rapid Colorimetric Assay for Cellular Growth and Survival: Application to Proliferation and Cytotoxicity Assays," *Journal of Immunological Methods* 65:55–63 (1983). Therefore, it was of interest to check whether the PDT effects were long lasting. The results of the experiments, in which HLE cells were tested for survival either 1 or 20 days (the same culture was split) following incubation with BPD (in 5% FCS or 25% Amvisc) and exposure to 10 $J/cm^2$ of red light showed a comparable cell kill (FIG. 5). This indicated that PDT effects are long lasting.

Figure 6A:
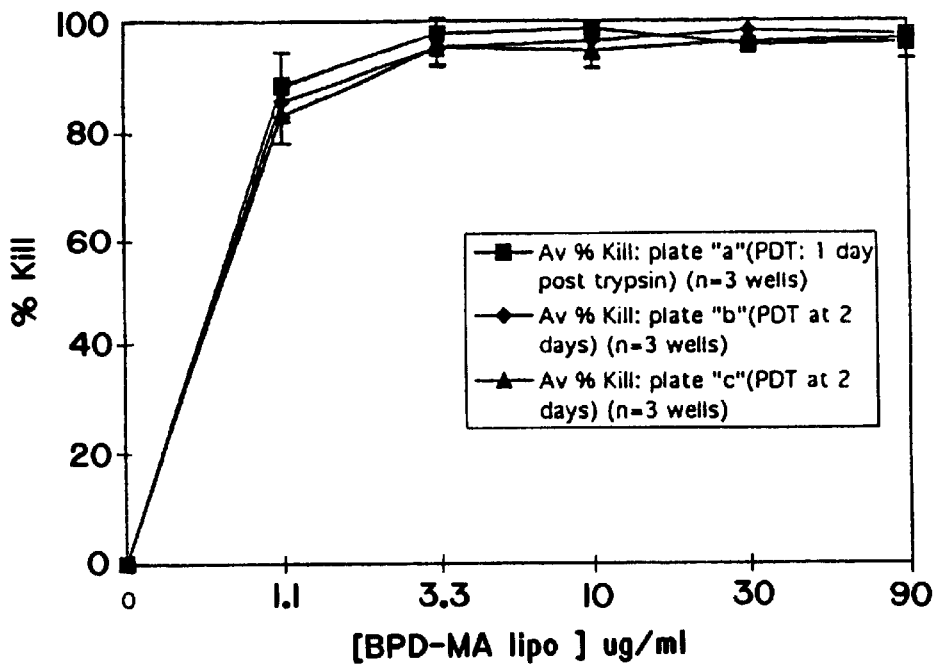
FIG. 6. shows the effect of a shortened incubation time with BPD.
Figure 6B:
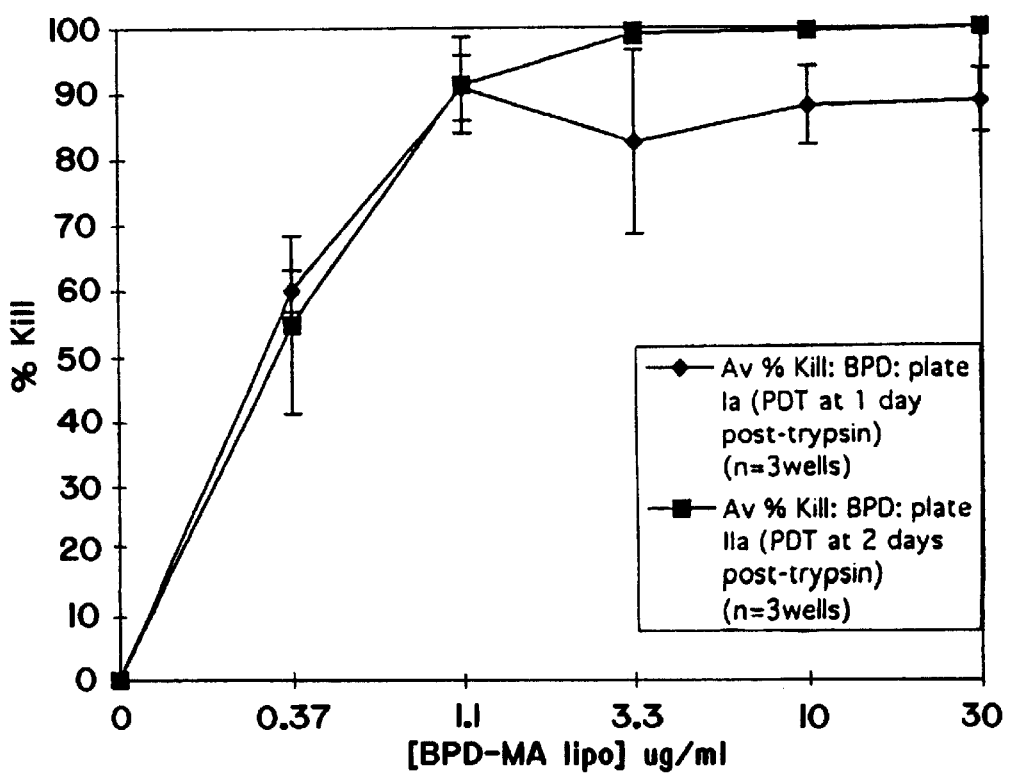

According to the opinions of cataract surgeons, even a 10 min. incubation time, considered appropriate at the beginning of the study, was unacceptably long. Thus, PDT effects were also tested following 1 min. incubation with BPD. The results of these experiments showed that, although BPD concentrations had to be increased from nannogram to microgram quantities per milliliter, a satisfactory cell kill was obtained (FIG. 6). One minute of cell contact with BPD at 3–5 µg/ml and 10 $J/cm^2$ of red light resulted in a very substantial cell kill. Some individual differences in cell sensitivity were observed (FIG. 6). Nevertheless, these concentrations are relatively low in pharmacological terms and could be readily optimized to a higher level resulting in a total cell kill. Rapid uptake by cells is very characteristic of BPD.

Figure 7A:
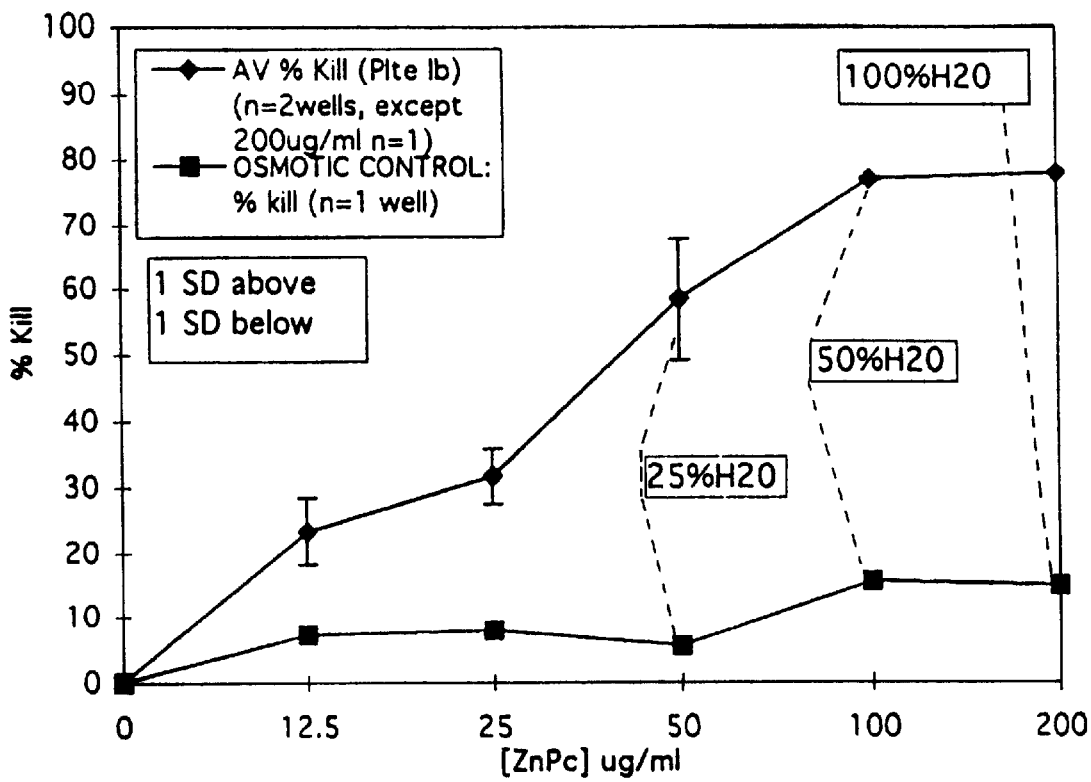
FIG. 7 shows the photosensitization of human lens epithelial cells with ZnPc.
Figure 7B:
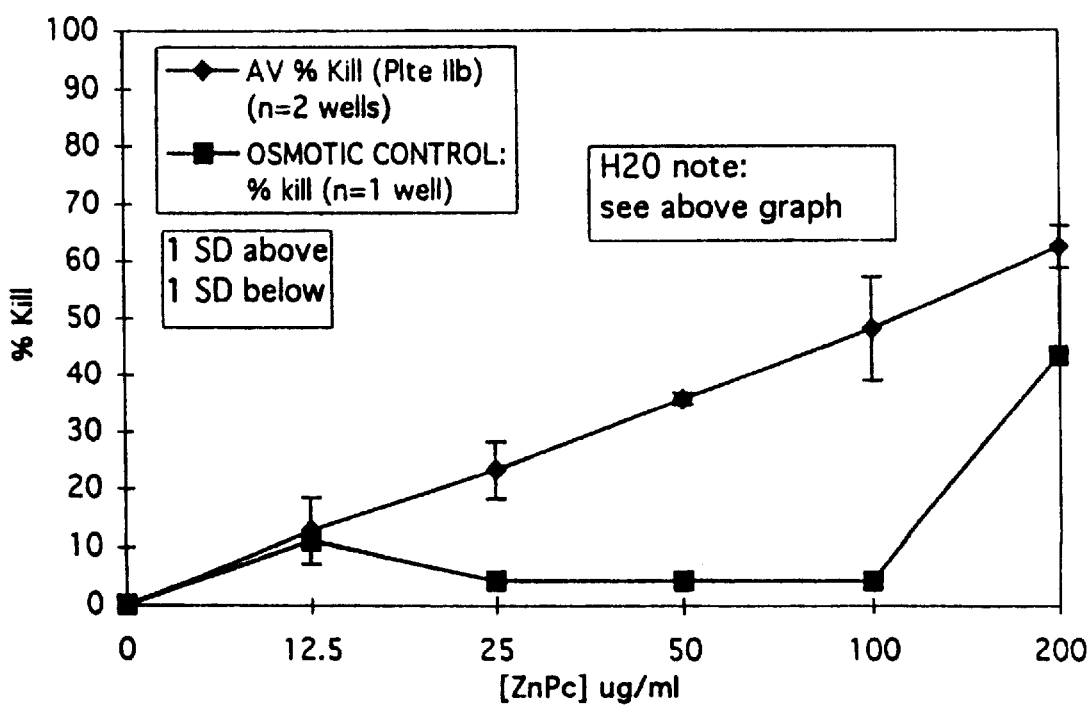

One other photosensitizer, ZnPc, was tested in this system (1 min. incubation, 10 $J/cm^2$ light). The highest concentration tested (200 µg/ml), which was limited by the concentration of the stock solution of ZnPc (200 µg/ml in water) resulted in maximum of 62–78% cell kill (FIG. 7).

EXAMPLE 3

Treatment of HLE Cells with BPD in a Viscous Solution

Figure 8A:
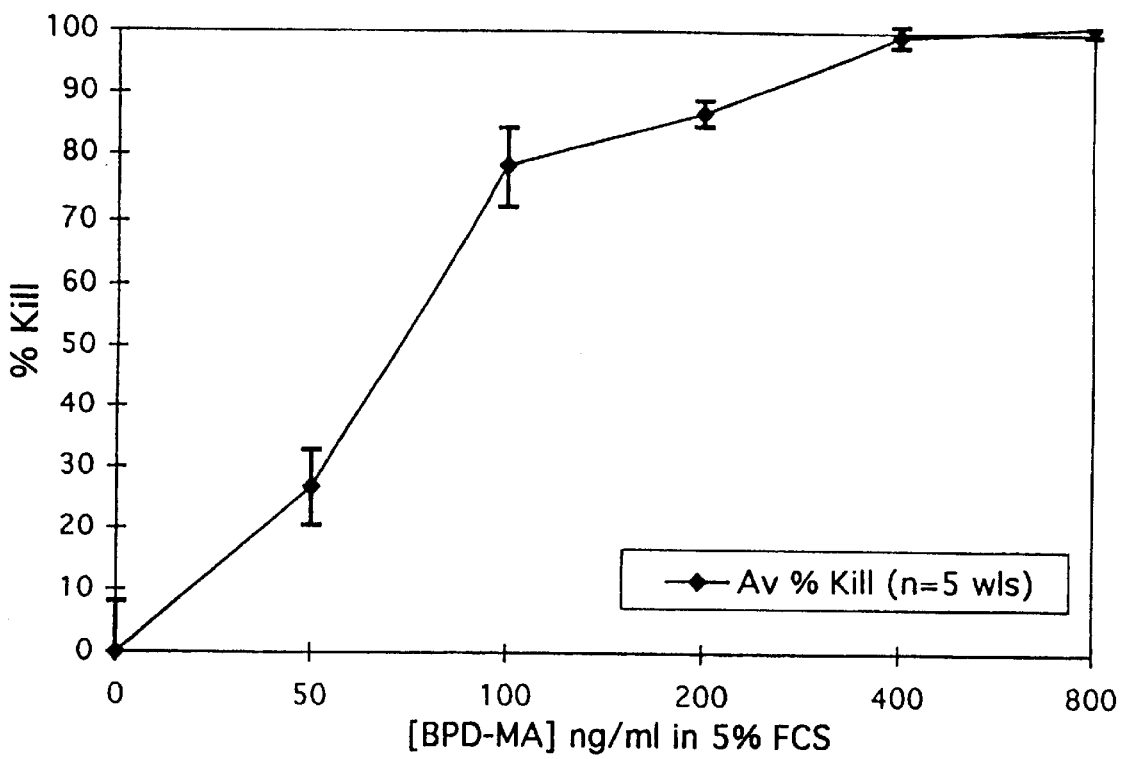
FIG. 8 shows the effect of BPD delivery in a viscous solution.
Figure 8B:
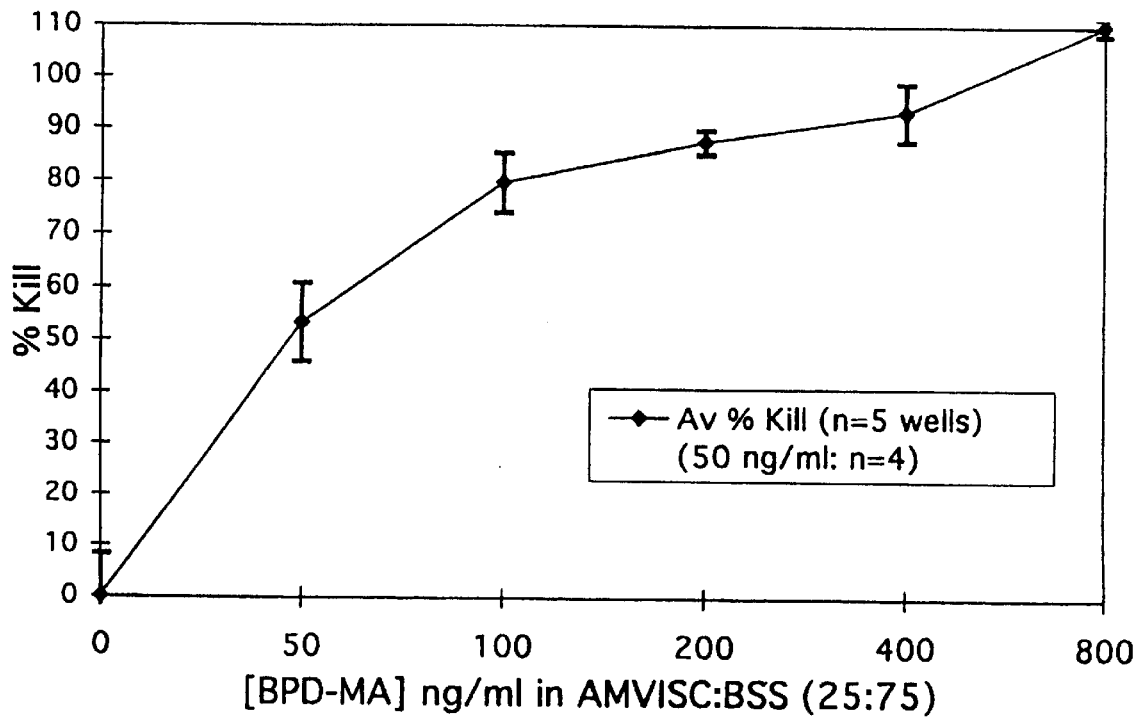

As noted above, optimally, in a clinical situation BPD will be delivered in a viscous solution. At present hydroxypropylmethyl cellulose (HPMC; Hymecel®) or sodium hyaluronate (SH; Amvisc, Ophthalin, Biolon) are appropriate reagents for this purpose and are known to those skilled in the relevant art. Therefore, the photosensitization of HLE cells with BPD delivered in viscous solution was evaluated in other vehicles. Due to its high viscosity, only 25% of Amvisc sodium hyaluronate in a balanced salt solution (BSS, as used in surgery) was tested in an HLE culture system and compared to the 5% FCS in culture medium of Example 2. Data showed that 10 min. incubation of HLE cells with BPD in either of the solutions, followed by 10 J/cm$^2$ of red light, caused a similar cell kill (FIG. 8). This indicates that BPD effectively can be delivered to cells when in viscous solution.

Figure 9:
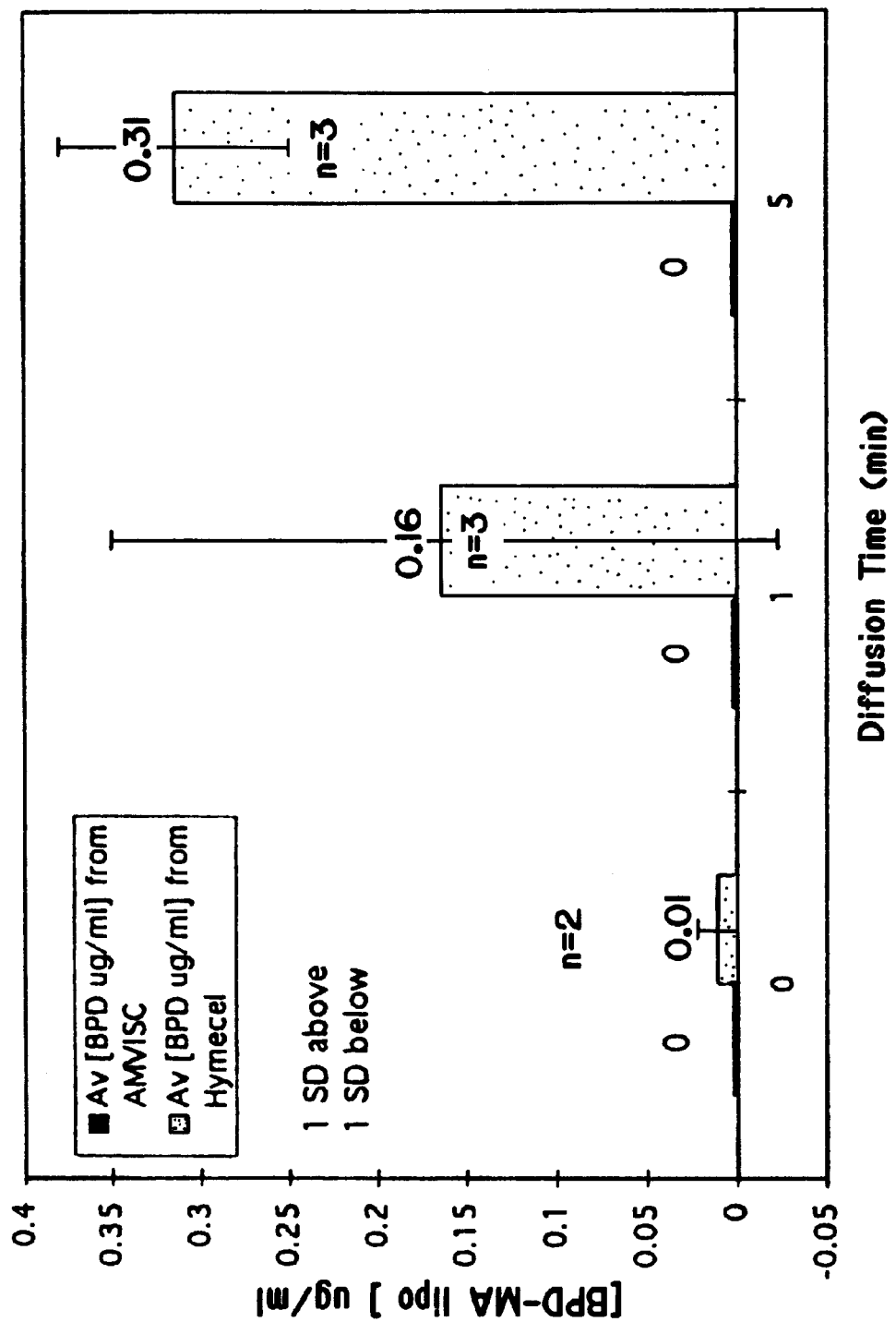
FIG. 9 shows the diffusion of BPD from either Amvisc or Hymecel into balanced salt solution.

The containment of BPD in the lens capsule and prevention of BPD contact with other ocular cells/tissues depends to some extent on its diffusion from viscous solution to either other drug-free viscous solution or balanced salt solution (BBS), both of which are used by surgeons to maintain the ocular pressure during the surgery. Preliminary experiments in vitro showed that BPD does not diffuse into BSS rapidly from either Hymecel or Amvisc, and much less from Amvisc than Hymecel (FIG. 9). Thus, Amvisc or any other sodium hyaluronate solution such as Ophthalin may be preferred vehicles for BPD. Rabbit lens capsules with epithelial cells still intact were also treated with BPD at 30 µg/ml in 100% Hymecel. These were incubated for 1 min. and exposed to 10 J/cm$^2$ of red light, resulting in a very high cell kill (FIG. 9).

EXAMPLE 4

Treatment of Vero Cells with BPD in a Viscous Solution

Figure 10A:
Figure 10B:
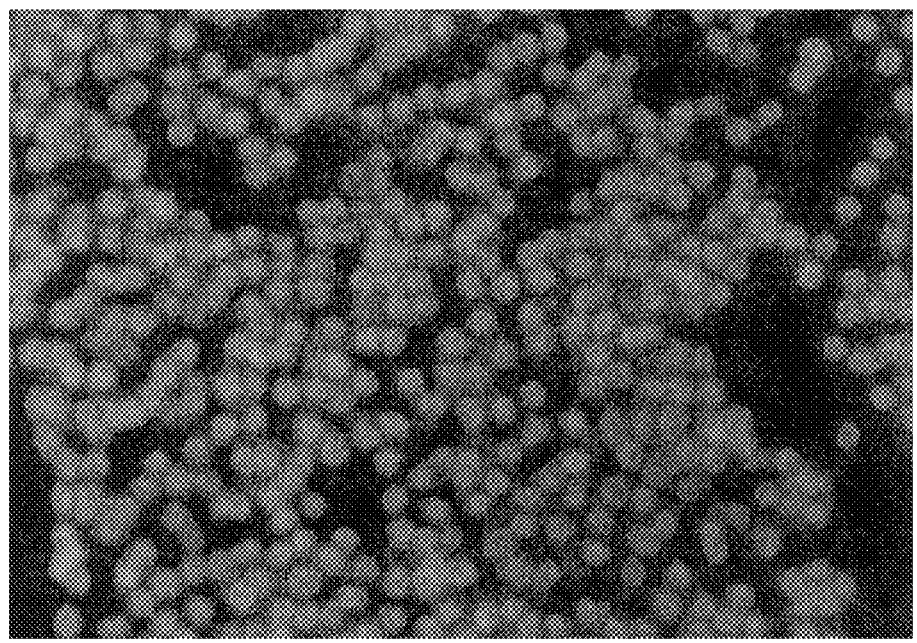
Figure 11A:
FIG. 11A shows untreated cells.
Figure 11B:
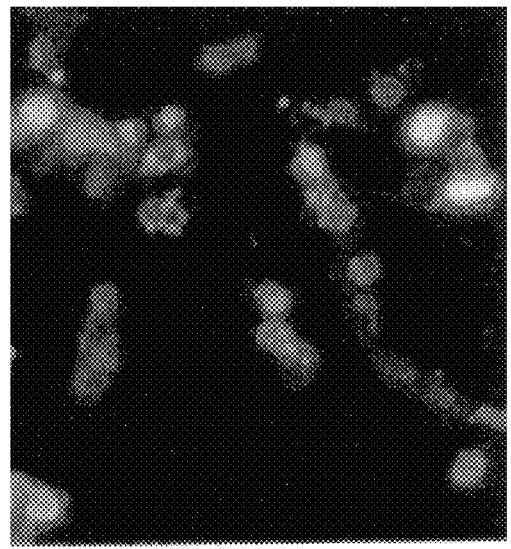
FIGS. 11B–D show various concentrations of BPD.
Figure 11C:
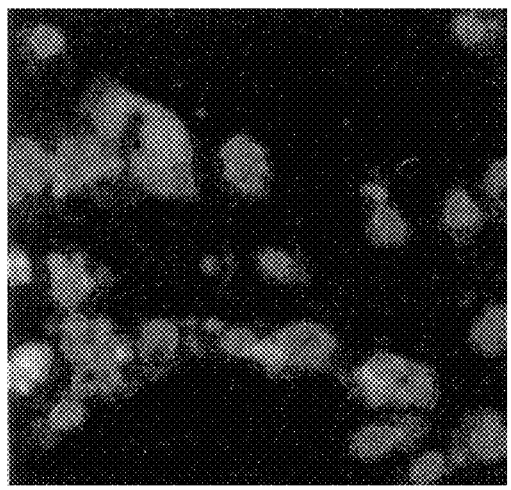
Figure 11D:
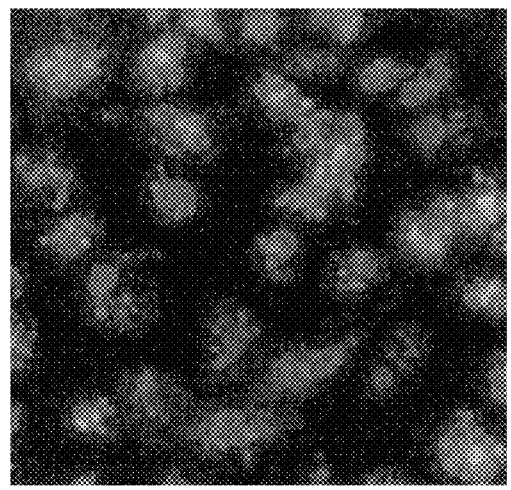

Due to difficulties in obtaining sufficient number of HLE cells for testing, some experiments were carried out using Vero cells as a model. The cells were grown on cover slips and treated with BPD in 100% viscous solution (Hymecel, Amvisc and Ophthalin). One minute incubation was used throughout, but light doses and BPD concentrations were varied. BPD was tested at 5–30 µg/ml using light doses of 1, 5 and 10 J/cm$^2$. Cell survival was determined by fluorescence, using a Cytoprobe Assay Kit (PerSeptive Bio Science; ethidium homodimer, and calcein-AM). Results indicating killing of HLE cells are presented in photographs (FIG. 10.)

EXAMPLE 5

Preparation of Ophthalmic Formulation A

Under aseptic and subdued light conditions, reconstitute a vial of liposomal BPD-MA (stock solution concentration of 2 mg/ml) with sterile water for injection. Take 0.1 ml of BPD-MA solution and add it to 1.9 ml of Ophthalin in a 3 ml glass syringe. At this stage, other components optionally can be added, such as agents to facilitate cell penetration or dyes for visualizing the formulation during the application in the eye. The excess air is removed, and the syringe is connected to another 3 ml glass syringe by means of a stainless steel luer connector. The BPD is mixed with the viscous material by pushing alternatively from one syringe to the other, and a minimum of approximately 30 pushes may be needed to obtain a homogenous formulation. The color of the final formulation is green and contains BPD-MA at a final concentration of about 0.1 mg/ml. A 20 gauge needle is attached to the syringe for administration, and the formulation is applied into the lens capsule, after removal of the lens, taking care to cover the equatorial region of the capsule.

EXAMPLE 6

Preparation of Ophthalmic Formulation B

Under aseptic and subdued light conditions, adjust the pH of a formulation of BPD-DA dissolved in PEG 400 (at a concentration of 10 mg/ml) to about neutral and then sterilize the formulation by filtration. Then, take 0.1 ml of the sterilized BPD-DA solution and add it to 1.9 ml of Ophthalin in a 3 ml glass syringe. At this stage, other components optionally can be added, such as agents to facilitate cell penetration or dyes for visualizing the formulation during the application in the eye. The excess air is removed, and the syringe is connected to another 3 ml glass syringe by means of a stainless steel luer connector. The BPD is mixed with the viscous material by pushing alternatively from one syringe to the other, and a minimum of approximately 30 pushes may be needed to obtain a homogenous formulation. The color of the final formulation is green and contains BPD-DA at a final concentration of about 0.5 mg/ml. A 20 gauge needle is attached to the syringe for administration, and the formulation is applied into the lens capsule, after removal of the lens, taking care to cover the equatorial region of the capsule.

EXAMPLE 7

In Vivo Application of Formulation A

The cytotoxic effect of the irradiation of the BPD-MA formulation of Example 5 with 690 nm light is investigated in vivo on rabbit lens epithelium. First, the rabbit eye to be treated is dilated and appropriate anesthesia is administered before the operation. The surgical procedure involves a cut at limbus (8 PM) and is made with a blade (anterior chamber stiletto knife, 0.9 mm, VISITEC). A balanced salt solution (BSS) is introduced through an anterior chamber maintainer, in order to keep the pressure in the anterior chamber constant (based on the height at which the container with BSS is placed over the rabbit's head). The pressure keeps the chamber slightly distended and the iris depressed giving better access to the capsule and more room for manipulation and homeostasis.

Next, another entry is made at limbus (12 AM), using a stiletto (0.9 mm in diameter) and a round anterior capsulectomy is made in the front part of the capsule using a bent 25G needle on a handle.

Using a 3 mm keratome the opening at 12 AM is enlarged. (This opening is used for entry of instruments into the anterior chamber and all manipulations.)

The phacoemulsifier is introduced next and the lens is systematically removed (this part of the procedure takes about 1–1.5 min). After phacoemulsification the cornea is covered with a drug-free viscous solution for protection from spilled BPD.

BPD in viscous solution is applied by systematic coating of the equatorial capsule wall, using the Raycroft cannula and a syringe. Special care is taken to cover the whole area, and especially the equatorial region.

Following incubation (1 min; longer times may be used), BPD is washed out using BSS from the anterior chamber maintainer and aspiration in the pupil and bag.

Theoretically, the light device should be introduced through the opening at 12 AM and it should be of such a shape as to allow its introduction into the capsule and irradiation mainly of the equatorial region with very limited illumination of the iris, cornea and retina (expected depth of the equatorial region from the front of the capsule with the anterior chamber maintainer (ACM)=1 mm).

Irradiation at 10 J/cm$^2$ is applied by laser diode for 30 seconds to kill remnant lens epithelial cells. The rest of the surgical procedure is completed per conventional protocols.

Based on the foregoing disclosure and exemplification, one skilled in the art could develop and utilize a variety of formulations appropriate to the prevention of secondary cataracts. Such formulations can utilize photosensitizing agents other than the green porphyrins, so long as the agents are rapidly taken up by remnant lens epithelial cells, their formulations can be substantially contained within the interior of the capsule and cause epithelial cell death upon the administration of a relatively brief exposure to an appropriate dose of light. Accordingly, the scope of the present invention is defined by the claims that follow, and not by the foregoing examples. All publications cited above are incorporated by reference.

We claim:

1. A pharmaceutical composition to prevent or inhibit the development of secondary cataracts, said composition comprising:

an amount of a green porphyrin effective to prevent or inhibit development of the secondary cataract when administered to a subject undergoing cataract surgery; and a pharmaceutically acceptable viscosity-increasing agent.

2. The composition of claim 1 wherein said viscosity-increasing agent is selected from the group consisting of hyaluronic acid and derivatives, starches and cellulose and its derivatives.

3. The composition of claim 1 wherein said effective amount of green porphyrin is a concentration in the range of about 0.2 to about 10 mg/ml in said composition.

4. The composition of claim 1 wherein said green porphyrin is formulated as a liposomal formulation.

5. The composition of claim 1 wherein said green porphyrin is of the formulas 1–6, as shown in FIG. 1, wherein $R^1$, $R^2$, $R^3$ and $R^4$ are noninterfering substituents.

6. The composition of claim 5 wherein $R^1$ and $R^2$ are independently carbomethoxy or carboethoxy.

7. The composition of claim 5 wherein each $R^3$ is —$CH_2CH_2COOH$ or a salt, amide, ester or acyl hydrazone thereof.

8. The composition of claim 5 wherein green porphyrin has the formula 3 or 4 in FIG. 1, wherein $R^4$ is a noninterfering substituent.

9. The composition of claim 5 wherein said green porphyrin is selected from the group consisting of BPD-DA, BPD-DB, BPD-MA and BPD-MB and their derivatives.

10. The composition of claim 9 wherein said green porphyrin is BPD-DA.

11. The composition of claim 1 wherein said green porphyrin is a BPD.

12. The composition of claim 1 further comprising a visible dye or enzyme.

* * * * *